United States Patent
Garcia et al.

(10) Patent No.: US 6,927,888 B2
(45) Date of Patent: Aug. 9, 2005

(54) METHOD AND APPARATUS FOR IMAGING USING POLARIMETRY AND MATRIX BASED IMAGE RECONSTRUCTION

(76) Inventors: Juan Manuel Bueno Garcia, Entremares 5, 3 D, Molina de Segura, Murcia, 30500 (ES); Melanie C. W. Campbell, 536 Clair Creek Blvd., Waterloo (CA), N2T 1R9

(*) Notice: Subject to any disclaimer, the term of this patent is extended or adjusted under 35 U.S.C. 154(b) by 17 days.

(21) Appl. No.: 10/436,365

(22) Filed: May 13, 2003

(65) Prior Publication Data

US 2004/0012853 A1 Jan. 22, 2004

Related U.S. Application Data

(60) Provisional application No. 60/379,417, filed on May 13, 2002, and provisional application No. 60/417,641, filed on Oct. 11, 2002.

(51) Int. Cl.[7] ............................................. G02B 26/08
(52) U.S. Cl. ....................... 359/196; 359/202; 359/371; 359/900; 356/369
(58) Field of Search ................................ 359/198–226, 359/368, 371, 385, 386, 391, 393, 900, 196, 197; 356/369, 239.7, 239.8; 351/200

(56) References Cited

U.S. PATENT DOCUMENTS 6,577,394 B1 * 6/2003 Zavislan ..................... 356/369

OTHER PUBLICATIONS

J. B. Pawley (Editor), Handbook of Biological Confocal Microscopy, 2nd ed. Plenum, New York (1995), (no copy furnished).

A. C. Ribes, S. Damaskinos, A. E. Dixon, K. A. Kellis, S. P. Duttagupta, and P. M. Fauchet, Progress in Surface Science, 50, 295 (1995).

R. H. Webb, G. W. Hughes, and F. C. Delori, Appl. Opt. 26, 1492 (1987).

J. Liang, D. R. Williams, and D. T. Miller, J. Opt. Soc. Am. A 14, 2884 (1997).

I. Iglesias and P. Artal. Opt. Lett. 25, 1804 (2000).

K. Muth, M.C.W. Campbell, A. J. Roorda, and C. Cui, OSA Technical Digest Series 1, 56–59 (1997).

M. P. Rowe, E. N. Pugh, Jr., J. S. Tyo, and N. Engheta, Opt. Lett. 20, 608 (1995).

Y. Gang and L. V. Wang, Opt. Lett. 24, 537 (1999).

S. Jiao Y. Gang and L. V. Wang, Appl. Opt. 39, 6318 (2000).

A. W. Dreher, K. Reiter, and R. N. Weinred, Appl. Opt. 31, 3730 (1992).

W. G. Egan, W. R. Johnson, and V. S. Whitehead, Appl. Opt. 30, 435 (1991).

W. Mickols, I Tinoco, J. E. Katz, M. F. Maestre, and C. Bustamente, Rev. Sci. Instrum. 12, 2228 (1985).

(Continued)

*Primary Examiner*—James Phan
(74) *Attorney, Agent, or Firm*—Lynn C. Schumacher; Hill & Schumacker

(57) ABSTRACT

The present invention provides a method and apparatus for improving the signal to noise ratio, the contrast and the resolution in images recorded using an optical imaging system which produces a spatially resolved image. The method is based on the incorporation of a polarimeter into the setup and polarization calculations to produce better images. After calculating the spatially resolved Mueller matrix of a sample, images for incident light with different states of polarization were reconstructed. In a shorter method, only a polarization generator is used and the first row of the Mueller matrix is calculated. In each method, both the best and the worst images were computed. In both reflection and transmission microscope and Macroscope and ophthalmoscope modes, the best images are better than any of the original images recorded. In contrast, the worst images are poorer. This technique is useful in different fields such as confocal microscopy, Macroscopy and retinal imaging.

40 Claims, 8 Drawing Sheets

OTHER PUBLICATIONS

R. A. Chipman, in *Handbook of Optics*, 2nd ed., M. Bass, ed. (McGraw–Hill, New York, 1995) Sec. 22.1.

J. M. Bueno and J. Jaronski, Opthal. Physiol. Opt. 21, 384 (2001).

J. M. Bueno and P. Artal, Opt. Lett. 24, 64 (1999).

H. G. Jerrard, J. Opt. Soc. Am. 44, 634 (1954).

J. W. Goodman, in *Laser Speckle and Related Phenomena*, 2nd ed., J.C. Dainty, ed., vol. 9 of Topics in Applied Physics (Springer–Verlag,1984), 9–75.

J. M. Bueno and P. Artal, J. Opt. Soc. Am A 18, 489 (2001).

B. Pelz, C. Weschenmoser, S. Goelz, J. P. Fischer, R. O. W. Burk, and J. F. Bille, Proc. SPIE 2930, 92 (1996).

* cited by examiner (a)

(b)

(c)

(a)

(b)

(c)

(a)

(b)

(c)

METHOD AND APPARATUS FOR IMAGING USING POLARIMETRY AND MATRIX BASED IMAGE RECONSTRUCTION

CROSS REFERENCE TO RELATED UNITED STATES PATENT APPLICATIONS

This patent application relates to U.S. Provisional patent application Ser. No. 60/379,417 filed on May 13, 2002, entitled CONFOCAL SCANNING LASER OPHTHALMOSCOPY IMPROVEMENT BY USING MUELLER-MATRIX POLARIMETRY, and U.S. Provisional patent application Ser. No. 60/417,641 filed on Oct. 11, 2002, entitled METHOD AND APPARATUS FOR IMAGING USING POLARIMETRY AND MATRIX BASED IMAGE RECONSTRUCTION.

FIELD OF THE INVENTION

This invention relates generally to a method of obtaining images of objects with optical systems using polarimetry and matrix based image reconstruction of the object, and more particularly the invention relates to obtaining images with a scanning laser optical system using Mueller-matrix polarimetry. This invention also relates to a method of obtaining images of the eye using scanning laser ophthalmoscopy, fundus photography or optical coherence tomography in combination with Mueller-matrix polarimetry.

BACKGROUND OF THE INVENTION

Image quality in any imaging system can often be limited by noise including speckle noise in coherent illumination, or by lower resolution or a lack of contrast due to scattered light or light from secondary light sources.

For more than four decades, confocal scanning laser microscopy has been used successfully to analyze samples in many diverse fields, ranging from biology[1] to the characterization of materials[2]. One type of scanning laser microscope with a large field of view is known as a Macroscope. This is an example of an instrument in which, for 1 scan direction, the sample is scanned relative to the beam. Webb and co-workers[3] presented the confocal scanning laser ophthalmoscope for viewing the ocular fundus, using the ocular optics as a microscope objective. Optical coherence tomography is also used generally to analyze samples and to image the ocular fundus. Images can be in 2 dimensions perpendicular to the optical beam incident on the sample, in a section with 1 dimension along the incident beam or in line scans in either of these two sections, and each of these modalities can be used to build up a 3 dimensional image of the object or the eye in depth. Since the optics of the eye degrade the image, additional improvements have been made to fundus imaging, such as adaptative optics[4], deconvolution techniques[5] or changes in the beam diameter and its entry position in the pupil of the eye[6]. The methodology outlined here can also be combined with a microscope (without beam scanning) with either confocal or non-confocal imaging.

The polarization properties of light have been used in conjunction with imaging techniques in target detection[7], optical coherence tomography[8,9], ophthalmologic diagnosis[10], remote sensing[11] and microscopy[12]. In general, optical imaging with polarization has been reported to improve contrast, reduce noise and provide useful information about scenes (not available with polarization-blind imaging). Structural information (for example nerve fiber layer thickness[10]) obtained from the polarization properties is also useful.

Confocal scanning laser ophthalmoscopy, scanning laser ophthalmoscopy and ocular optical coherence tomography are used for the diagnosis of eye diseases and disorders that affect structures at the rear of the eye and for basic scientific and biomedical investigations of these structures. Confocal scanning laser microscopy is used to characterize many materials and for biomedical investigations, including the diagnosis of disorders and diseases of the cornea of the eye. Major limitations to the recognition of features limit diagnosis and evaluation of structures viewed in confocal scanning laser ophthalmoscopy, in confocal scanning laser microscopy and in optical coherence tomography. These limitations include pixel to pixel noise, lowered contrast and a lack of resolution. A lowering of contrast and an increase in the size of the features resolved is partly due to the imperfect optical quality of the objective that in the case of ophthalmoscopy and ocular optical coherence tomography is the eye itself. Noise can be increased due to imperfect optics or due to a lower signal reflected from the structures being observed, reducing the signal to noise ratio. However, these reductions in contrast, resolution and signal to noise ratio are a function of the polarization properties of the features being imaged.

Therefore, it would be very advantageous to provide a method which provides improved image contrast, image resolution and/or the signal to noise ratio of a given image.

SUMMARY OF THE INVENTION

This is achieved in part by providing a method of obtaining images of an object where the object is illuminated by incident beam(s) of selectively polarized light and the images reflected (or transmitted) for each different incident beam polarization is recorded using methods which resolve individual image points from the object. Matrix methods are used to reconstruct multiple images from the recorded image signals and the best image selected.

In one aspect of the present invention there is provided a method for producing images of an object or region of interest of the object, comprising the steps of:

a) producing an incident beam of light in a pre-selected polarization state and scanning said incident beam of light point by point across and/or along an object or region of interest of the object;

b) detecting light intensity signals corresponding to beams of light in a pre-selected number of polarization states reflected or transmitted point by point from the object or region of interest of the object and storing electronic signals corresponding to the detected light intensity signals;

c) repeating steps a) and b) for an effective number of pre-selected polarization states of the incident beam of light;

d) constructing a spatially resolved matrix of the object point by point from the detected light intensity signals and from said spatially resolved matrix constructing spatially resolved images of the object or region of interest of the object for a set of theoretical polarization states of the incident beam of light in addition to those input states generated in the incident beam of light, said matrix being selected to describe the effect of the object on the polarization properties of light;

e) characterizing image quality of each image in accordance with an effective image quality parameter and based upon said characterization selecting a best image of said object or region of said object; and f) visually displaying said best image.

In this context, by object, we mean the part of the object between the input beam and the detector—if the light is being reflected from a plane that is within the object, this would be the effect of the light passing through the object in front of the reflecting plane twice. If we are measuring transmitted light, this is would be the full thickness of the object, whose polarisation matrix might depend on the focal plane of the light, In the case of a confocal or optical coherence tomography system in reflection, where we will image as a function of depth location, the matrix of the object could either represent the full thickness to the current image plane or we could calculate out the matrix of the tissue in front of the current imaging plane (in the case where we take 16 samples).

The present invention also provides a method for producing images of an object or region of interest of the object, comprising the steps of:

a) producing an incident beam of light in a pre-selected polarization state and scanning said incident beam of light point by point across an object or region or along an object or a region of interest of the object;

b) detecting light intensity signals corresponding to beams of light reflected or transmitted point by point from the object or region of interest of the object and storing electronic signals corresponding to the detected light intensity signals;

c) repeating steps a) and b) for an effective number of pre-selected polarization states of the incident beam of light;

d) constructing a spatially resolved vector of the object point by point from the detected light intensity signals and from said spatially resolved vector constructing spatially resolved images of the object or region of interest of the object for a set of theoretical polarization states of the incident beam of light in addition to those input states generated in the incident beam of light, said vector comprised of independent elements of a matrix being selected to describe the effect of the object on the polarization properties of light;

e) characterizing image quality of each image in accordance with an effective image quality parameter and based upon said characterization selecting a best image of said object; and f) visually displaying said best image.

In another aspect of this invention there is provided a method for producing images of an object or region of interest of the object, comprising the steps of:

a) producing an incident beam of light in a pre-selected polarization state and illuminating an object or region of interest of the object with the selectively polarized beam of light;

b) detecting an array of light intensity signals reflected from spatially distinct points of the object or region of interest of the object and storing electronic signals corresponding to said detected array of light signals;

c) repeating steps a) and b) for an effective number of pre-selected polarization states of the incident beam of light;

d) constructing a spatially resolved vector comprised of independent elements of a spatially resolved matrix of the object point by point from the detected light intensity signals and from said spatially resolved vector constructing spatially resolved images of the object or region of interest of the object for a set of theoretical polarization states of the incident beam of light in addition to those input states generated in the incident beam of light, said matrix being selected to describe the effect of the object on the polarization properties of light;

e) characterizing image quality of each image in accordance with an effective image quality parameter and based upon said characterization selecting a best image of said object; and f) visually displaying said best image.

The present invention also provides a method for producing images of an object or region of interest of the object, comprising the steps of:

a) producing an incident beam of light in a pre-selected polarization state and scanning said incident beam of light point by point across an object or region or along an object or a region of interest of the object by moving the object with respect to the incident beam or by moving the object in 1 dimension with respect to the incident beam and scanning the beam in a perpendicular direction with respect to the object;

b) detecting light intensity signals corresponding to beams of light reflected or transmitted point by point from the object or region of interest of the object and storing electronic signals corresponding to the detected light intensity signals;

c) repeating steps a) and b) for an effective number of pre-selected polarization states of the incident beam of light;

d) constructing a spatially resolved vector of the object point by point from the detected light intensity signals and from said spatially resolved vector constructing spatially resolved images of the object or region of interest of the object for a set of theoretical polarization states of the incident beam of light in addition to those input states generated in the incident beam of light, said vector comprised of independent elements of a matrix being selected to describe the effect of the object on the polarization properties of light;

e) characterizing image quality of each image in accordance with an effective image quality parameter and based upon said characterization selecting a best image of said object; and f) visually displaying said best image.

In another aspect of the invention there is provided a method for producing images of an object or region of interest of the object, comprising the steps of:

a) producing an incident beam of light in a pre-selected polarization state and illuminating an object or region of interest of the object with the selectively polarized beam of light;

b) detecting an array of light intensity signals corresponding to beams of light in a pre-selected number of polarization states reflected from spatially distinct points of the object or region of interest of the object and storing electronic signals corresponding to said detected array of light signals;

c) repeating steps a) and b) for an effective number of pre-selected polarization states of the incident beam of light;

d) constructing a spatially resolved matrix of the object from the detected light intensity signals and from said spatially resolved matrix constructing spatially resolved images of the object or region of interest of the object for a set of theoretical polarization states of the incident beam of light in addition to those input states generated in the incident beam of light, said matrix being selected to describe the effect of the object on the polarization properties of light;

e) characterizing image quality of each image in accordance with an effective image quality parameter and based upon said characterization selecting a best image of said object; and f) visually displaying said best image.

The present invention also provides a method for producing images of an object using confocal scanning laser microscopy or nonconfocal or non-scanning, comprising the steps of:

a) calibrating a confocal scanning laser microscope modified to include a polarization generator and a polarization analyzer to obtain a Mueller matrix $$M_{SCN}^{(1)},$$

of the instrument in the incoming direction, wherein a matrix of 16 intensity values results from intensity measurements with a rotating ¼ wave plate located in said generator positioned in each of four positions including 45 degrees, 0 degrees, 30 degrees and 60 degrees, while a ¼ wave plate located in said analyzer is placed in each of the same four positions;

b) calibrating said modified confocal scanning instrument to obtain a Mueller matrix $$M_{SCN}^{(2)},$$

of the instrument in the outgoing direction, wherein a matrix of 16 intensity values results from intensity measurements with a rotating ¼ wave plate located in said generator positioned in each of four positions including 45 degrees, 0 degrees, 30 degrees and 60 degrees, while a ¼ wave plate located in said analyzer is placed in each of the same four positions;

c) placing said object in said modified confocal scanning apparatus and focusing light onto said object and recording sixteen gray scale images with the object in place for each of four generator states with a ¼ wave plate at 45, 0, 30 and 60 degrees combined with each of the four analyzer states ¼ wave plate at 45, 0, 30 and 60 degrees;

d) placing said sixteen grey scale values for each pixel into a spatially resolved matrix, $I^{(mn)}$, which is a first element of a Stokes vector, $$S_D^{(mn)}$$

reaching the photodetector;

e) from $I^{(mn)}$ calculate $M_{out}$ from equation 2, given by $$\begin{pmatrix} I^{(1\_1)} & I^{(2\_1)} & I^{(3\_1)} & I^{(4\_1)} \\ I^{(1\_2)} & I^{(2\_2)} & I^{(3\_2)} & I^{(4\_2)} \\ I^{(1\_3)} & I^{(2\_3)} & I^{(3\_3)} & I^{(4\_3)} \\ I^{(1\_4)} & I^{(2\_4)} & I^{(3\_4)} & I^{(4\_4)} \end{pmatrix} = M_A \cdot M_{OUT};$$

f) from equation 3, given by $$M = (M_{SCN}^{(2)})^{-1} \cdot M_{OUT} \cdot (M_G)^{-1} \cdot (M_{SCN}^{(1)})^{-1},$$

calculate M, the spatially resolved Mueller matrix of the object;

g) choosing values of an incident Stokes vector, $S_{IN}$, around a Poincaré sphere in predetermined increments of $\chi$ and $\phi$ which represent, respectively, the azimuth and ellipticity of the incident Stokes vector on the Poincaré sphere;

h) applying equation 4, given by $$S_D^{(mn)} = \overline{M}_A^{(n)} \cdot M \cdot M_{SCN}^{(1)} \cdot S_G^{(m)},$$

to reconstruct images, $I^{(out)}$, pixel by pixel for each incident Stokes vector;

i) for each image, calculate the image quality measure of choice, for example SNR as defined in equation 7, given by $$SN = (SNR)^{-1} = \frac{stdv(I^{(out)})}{\text{mean}(I^{(out)})};$$

and j) display the image with best value of the image quality measure.

The present invention also provides a method for producing images of an object using scanning laser microscopy (or macroscopy), in transmission mode comprising the steps of:

a) calibrating a scanning laser microscope or macroscope modified to include a polarization generator and a polarization analyzer to obtain a Mueller matrix $$M_{SCN}^{(1)},$$

of the instrument in the incoming direction, wherein a matrix of 16 intensity values results from intensity measurements with a rotating ¼ wave plate located in said generator positioned in each of four positions including 45 degrees, 0 degrees, 30 degrees and 60 degrees, while a ¼ wave plate located in said analyzer is placed in each of the same four positions;

b) placing said object in said modified confocal scanning apparatus and focusing light onto said object and recording sixteen gray scale images with the object in place for each of four generator states with a ¼ wave plate at 45, 0, 30 and 60 degrees combined with each of the four analyzer states ¼ wave plate at 45, 0, 30 and 60 degrees;

c) placing said sixteen grey scale values for each pixel into a spatially resolved matrix, $I^{(mn)}$, which is a first element of a Stokes vector, $$S_D^{(mn)}$$

reaching the photodetector, d) from $I^{(mn)}$ calculate $M_{out}$ from equation 2, given by $$\begin{pmatrix} I^{(1\_1)} & I^{(2\_1)} & I^{(3\_1)} & I^{(4\_1)} \\ I^{(1\_2)} & I^{(2\_2)} & I^{(3\_2)} & I^{(4\_2)} \\ I^{(1\_3)} & I^{(2\_3)} & I^{(3\_3)} & I^{(4\_3)} \\ I^{(1\_4)} & I^{(2\_4)} & I^{(3\_4)} & I^{(4\_4)} \end{pmatrix} = M_A \cdot M_{OUT};$$

e) from equation 5, given by $$M = M_{OUT} \cdot (M_G)^{-1} \cdot (M_{SCN}^{(1)})^{-1},$$

calculate M, the spatially resolved Mueller matrix of the object;

f) choosing values of an incident Stokes vector, $S_{IN}$, around a Poincaré sphere in predetermined increments of $\chi$ and $\phi$ which represent, respectively, the azimuth and ellipticity of the incident Stokes vector on the Poincaré sphere;

g) applying equation 6, given by $$\begin{pmatrix} I^{(OUT)} \\ S_1^{(OUT)} \\ S_2^{(OUT)} \\ S_3^{(OUT)} \end{pmatrix} = \begin{pmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{pmatrix} \cdot \begin{pmatrix} 1 \\ \cos(2\chi) \cdot \cos(2\varphi) \\ \sin(2\chi) \cdot \cos(2\varphi) \\ \sin(2\varphi) \end{pmatrix}$$

$$= M \cdot S_{IN},$$

to reconstruct images, $I^{(out)}$, pixel by pixel for each incident Stokes vector;

h) for each image, calculating the image quality measure of choice, for example SNR as defined in equation 7, given by $$SN = (SNR)^{-1} = \frac{stdv(I^{(out)})}{mean(I^{(out)})};$$

and i) displaying the image with best value of the image quality measure.

The present invention also provides an optical scanning apparatus for producing images of an object, comprising:

a) a light source for producing a light beam;

b) polarization generator means for producing selected polarization states in the light beam upon passage of the light beam through said polarization generator means to produce a selectively polarized light beam;

c) scanning means for receiving the selectively polarized light beam and spatially scanning the selectively polarized light beam in two dimensions across an object point by point or alternately scanning the sample with respect to the laser beam or scanning the beam in 1 or 2 dimensions and the sample in the perpendicular direction;

d) polarization analyzer means for transmitting light beams of selected polarization, including directing and focusing optics for directing the reflected light beams reflected point by point from the object to said polarization analyzer means;

e) detection means and light shaping and focusing means for directing and focusing the reflected light beams of selected polarization onto said detection means;

f) computer processing means connected to said detection means, said computer processing means including image analysis means for processing signals from said detector due to the reflected light beams of selected polarization detected by said detection means and producing therefrom images of the object; and g) display means for displaying an image of the object produced by said processing means.

BRIEF DESCRIPTION OF THE DRAWINGS

Preferred embodiments of the invention will now be described, by way of example only, with reference to the drawings, in which:

FIG. 4(a) shows the worst reconstructed image, FIG. 4(b) shows the best original image, FIG. 4(c) shows the best reconstructed image;

FIG. 8(a) shows the best original image.

DETAILED DESCRIPTION OF THE INVENTION

Figure 1:
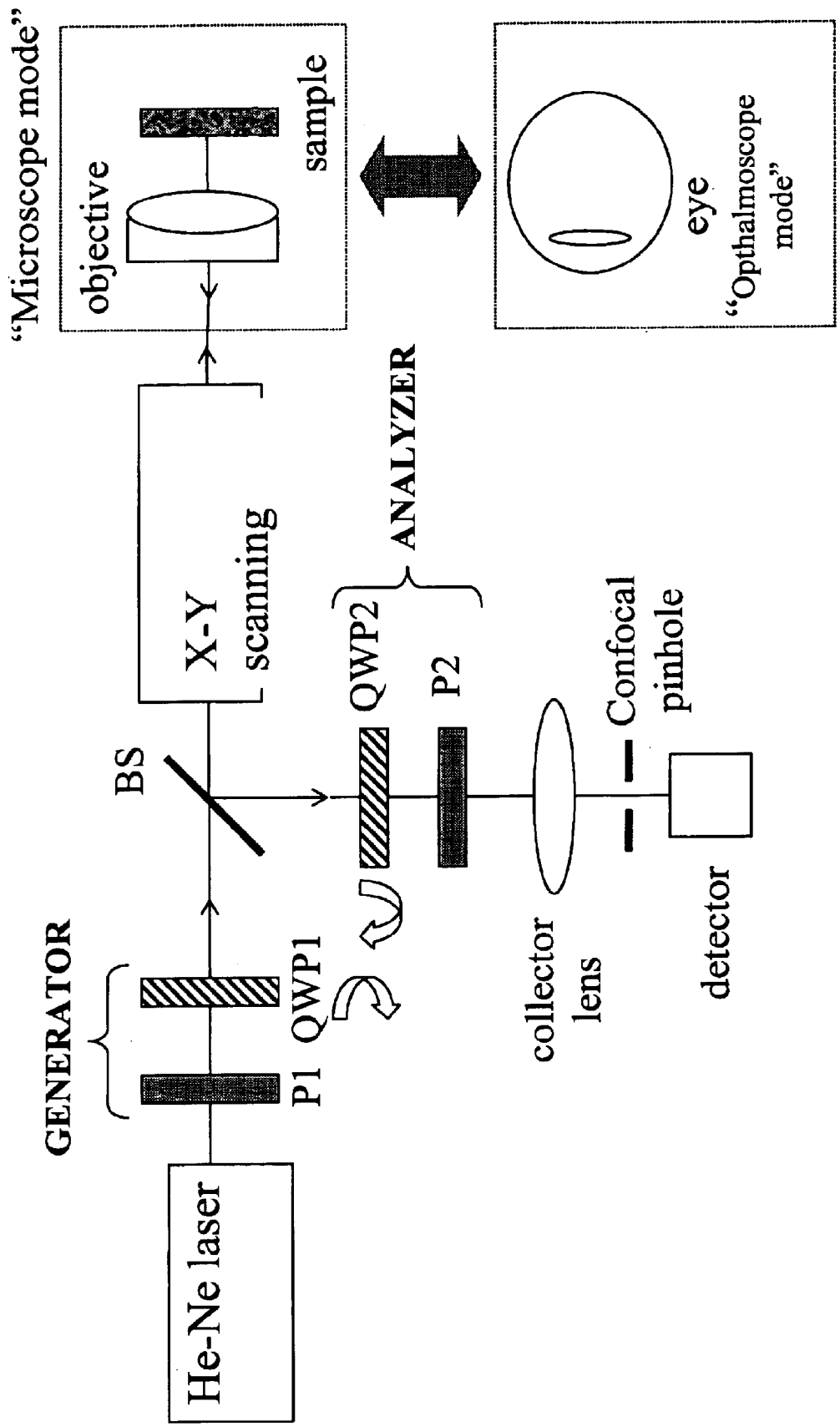
FIG. 1 shows a block diagram of an apparatus used to perform the method of the present invention in which P1 and P2, linear horizontal polarizers; QWP1 and QWP2, rotating quarter-wave plates wherein both microscope configuration (viewing the object) and ophthalmoscope configuration (viewing a person's eyeball) are shown.

Broadly, the present invention provides a method of obtaining images of an object where the object is illuminated by incident beam(s) of selectively polarized light or nonpolarized light and the images reflected or transmitted by the object for each different incident beam polarization is analised with respect to its polarization and then recorded using methods which resolve individual image points from the object. Matrix methods are used to reconstruct multiple images from the recorded image signals and the best image selected.

The method may be implemented using an optical scanning system or a scanning stage on which the object is placed such as for example a scanning laser system. The scans may be 2 dimensional in any combination of 2 perpendicular axes or 3 dimensional. In one embodiment the method and apparatus use Mueller-matrix polarimetry to reduce noise and improve images of light reflected from the sample recorded with the optical scanning system. In a second embodiment the method and apparatus use Mueller-matrix polarimetry to reduce improve image resolution and contrast of images of light transmitted by the sample recorded by a combination of optical scanning and sample scanning.

The image improvement includes improvements in the signal-to-noise ratio, an improvement in contrast across local features and an improvement in the resolution of features (visibility of small details).

Since different objects or different regions of interest of an object have different polarization properties, the analysis gives an improved image corresponding to a different incoming polarization state on the Poincaré sphere dependent on these properties.

Improvements have been shown for both specularly and diffusely reflecting objects, for light transmitted by objects and for an object (the fundus) which produces a combination of diffuse, specular and directional reflections.

The analysis disclosed hereinafter is spatially resolved, that is, it is performed on a pixel by pixel basis, so that the improvements in images of different areas of the object depend on the local polarization properties of the object, and the calculation described herein may produce a different best image of each object area of interest.

The analysis depends on the measure of best image quality used, so that the best image produced may depend on the measure used. However, in some of the examples given below, a signal to noise (SNR) maximum measure across a large area of the image gives the best image defined by the signal to noise ratio measure used. It also produced images with higher contrast of local features and higher resolution of fine detail. So initially, a SNR measure appears to be the best image quality measure for example when laser speckle is present. When small details need to be resolved, a contrast measure appears to be the best image quality measure.

The method can be used to give the best image quality for other image quality measures including those that combine contrast, SNR and resolution measures if necessary.

One embodiment of the method is based on the incorporation of a polarimeter into a laser scanning system combined with a specialized spatially resolved calculation and image display. After calculating the spatially resolved Mueller matrix of a sample, images for incident light with different states of polarization are reconstructed with increments chosen of 1 degree for azimuth and ellipticity over the Poincaré sphere. The increments over the Poincaré sphere chosen in the calculation could be varied. The calculation generates images for incoming polarization states that could not be generated in the experimental imaging system. The best computed image in both reflected light microscope and ophthalmoscope modes as well as in transmission Macroscope mode, are better than any of the original images recorded with polarimetry. In contrast, the worst computed images are poorer.

Referring to FIG. 1, a schematic diagram of a confocal scanning microscope modified to include a polarimeter[13] is shown generally at 10 with the polarimeter comprising a generator unit 12 which includes a fixed linear polarizer P1 and a rotating ¼-wave plate QWP1. The apparatus includes an analyzer 14 in a symmetric configuration with respect to the generator 12 which comprises a fixed linear polarizer P2 and a rotating ¼-wave plate QWP2 in the analyzer unit. The system 10 may be used in both microscope and ophthalmoscope modes. In the microscope mode, the focal length and the numerical aperture for the objective lens 16 was 90 mm and 0.11 respectively but it will be understood that different objective lenses may be used. In the ophthalmoscope mode, the patient's eye itself acted as a microscope objective. A 633-nm He—Ne laser 18 is used as the light source and a photo-multiplier tube as the detector but those skilled in the art will appreciate that other light sources or photodetectors may be used, either in a modified commercial microscope or commercial ophthalmoscope or in a customized design.

An X-Y scanning system 30 permits the light beam to be scanned across the sample or inside or outside of the eyeball of the patient in a raster. Any commercially available raster scan system, or application specific system or any novel system may be used including resonance scanners, galvonometer scanners, oscillating mirrors, acosto-optic deflectors, solid state deflectors, single facet or polygon rotating mirrors, holographic scanners or micro-electro mechanical scanners. The beam splitter BS directs information bearing light beam reflected from the sample or eyeball through the collector lens 28 through confocal pinhole 26 onto the detector 22.

The laser beam is scanned in two dimensions and focused on the sample (a target or the retina) by the objective or the ocular optics. The light reflected back from the sample at each point of the scan is recorded by the detector 22. In studies conducted by the inventors the size of the light beam entering the objective 16 (and the eye) was 2.5 mm and the confocal pinhole 26 was 600 microns in diameter. The focal length of the collector lens 28 was 50 mm. The system records images at a rate of 28.5 Hz. However it will be appreciated that these variables are exemplary only and may be varied by those skilled in the art.

Figure 6:
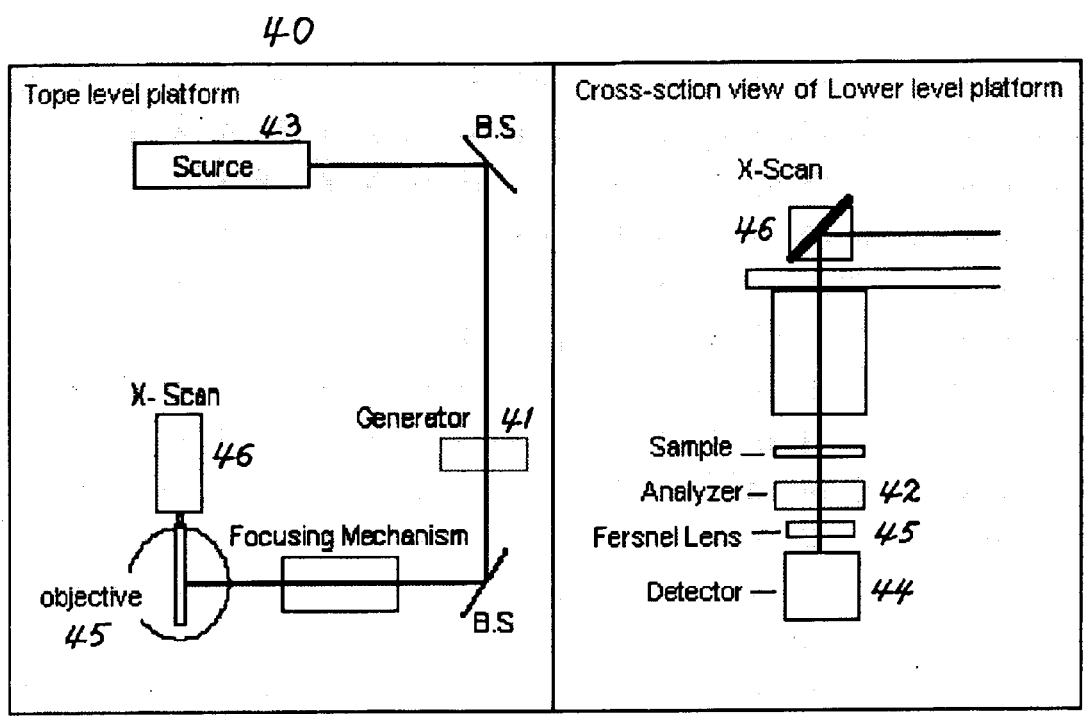
FIG. 6 shows the block diagram of a commercially available Macroscope, used to perform the method of the present invention in which the generator consists of a linear horizontal polarizer and a rotating quarter-wave plate and the analiser consists of a linear horizontal polarizer and a rotating quarter-wave plate.

Referring to FIG. 6, a schematic diagram of a scanning Macroscope in transmission mode modified to include a polarimeter[13] is shown generally at 40 with the polarimeter comprising a generator unit 41 which includes a fixed linear polarizer and a rotating ¼ wave plate. The apparatus includes an analyzer 42 in a symmetric configuration with respect to the generator which comprises a fixed linear polarizer and a rotating ¼ wave plate in the analyzer unit. A wide angle telecentric lens 45 is used in the Macroscope but it will be understood that different objective lenses may be used in a Macroscope or microscope configuration. A 633-nm He—Ne laser is used as the light source 43 and a photo-multiplier tube as the detector 44 but those skilled in the art will appreciate that other light sources or photodetectors may be used, either in a modified commercial microscope or in a customized design.

A linear scanning system 46 permits the light beam to be scanned across the sample and is combined with a stage moving in a perpendicular direction to create a raster scan of the object. Any commercially available raster scan system, or application specific system or any novel system may be used including resonance scanners, galvonometer scanners, oscillating mirrors, acosto-optic deflectors, solid state deflectors, single facet or polygon rotating mirrors, holographic scanners or micro-elctro mechanical scanners or any mechanical means of scanning the beam and or stage in 1 or 2 dimensions. The information bearing light beam transmitted by the sample goes through the collector lens 45 onto the detector.

The laser beam is focused on the sample by the objective. The light transmitted by the sample at each point of the scan is recorded by the detector. However it will be appreciated that the variables used here are exemplary only and may be varied by those skilled in the art.

The sixteen (16) combinations of polarization states required to calculate the Mueller matrix for each point of the scanned sample correspond to different angles of the fast axes of the two rotating quarter-wave plates QWP1 and QWP2 as previously described[14]. The generator 12 and analyzer 14 in FIG. 1 and in FIG. 6 may be connected to computer controlled mechanical actuator system (not shown) for moving the ¼ wave plates QWP1 and QWP2 into the four different positions. Alternately, fast electro-optical devices (including but not limited to liquid-crystals, photoelastic modulators) could be used to vary the polarization states of the generator and analyser[15].

The system is calibrated by taking a measurement in the incoming pathway. This will give the Mueller matrix, $$M_{SCN}^{(1)},$$

of the instrument in the incoming direction. A matrix of 16 intensity values results from intensity measurements with the generator's rotating ¼ wave plate in each of four positions −45 degrees, 0 degrees, 30 degrees and 60 degrees, while the analyzer's ¼ wave plate is placed in each of the same four positions.

The outgoing direction of the instrument in FIG. 1 is also calibrated. This will give the Mueller matrix, $$M_{SCN}^{(2)},$$

of the instrument in the outgoing direction. A matrix of 16 intensity values results from intensity measurements with the generator ¼ wave plate QWP1 in each of four positions described previously while the analyzer ¼ wave plate QWP2 is placed in each of the same four positions.

Sixteen (16) gray scale images are taken with the object in place for each of the four generator states (¼ wave plate QWP1 at 45, 0, 30 and 60 degrees) combined with each of the same four analyzer states (¼ wave plate QWP2 set at 45, 0, 30 and 60 degrees while QWP1 is in each of its fours states). The generator produces polarized light at a particular orientation, set by a linear polarizer P1 and the QWP1. The analyser composed of QWP2 and the linear polarizer P2 turns light of a particular polarization into linearly polarized light.

The 16 grey scale values for each pixel are placed into a spatially resolved matrix, $I^{(mn)}$ which is the first element of the Stokes vector, $$S_D^{(mn)}$$

reaching the photodetector.

For every Stokes vector $$S_G^{(m)} \ (m = 1, 2, 3, 4)$$

produced by the generator, the intensity reaching the detector for each point of the sample ($I^{(mn)}$), is the first element of the Stokes vector $$S_D^{(mn)} \ (m = 1, 2, 3, 4)$$

given by:

$$S_D^{(mn)} = \overline{M}_A^{(n)} \cdot M_{SCN}^{(2)} \cdot M \cdot M_{SCN}^{(1)} \cdot S_G^{(m)} \quad (1)$$

where $M = M_{ij}$ (i, j=0, 1, 2, 3) is the Mueller matrix of the sample under study, $$\overline{M}_A^{(n)}$$

is one of the four Mueller matrices of the analyzer unit (each corresponding to an independent state), and $$M_{SCN}^{(1)} \text{ and } M_{SCN}^{(2)}$$

are the Mueller matrices of the experimental system itself (lenses, scanning unit and beam splitter) for first and second passages respectively, previously measured in the calibration process. For each generator-analyzer combination, the image is spatially resolved, giving a spatially resolved M. Let $M_A$ be the 4×4 auxiliary matrix with each row being the first row of every $$\overline{M}_A^{(n)} \text{and } M_{OUT} = [S_{OUT}^{(1)}, S_{OUT}^{(2)}, S_{OUT}^{(3)}, S_{OUT}^{(4)}]$$

be another auxiliary matrix with $$S_{OUT}^{(m)}$$

each Stokes vector going into the analyzer unit. These matrices are then related:

$$\begin{pmatrix} I^{(1\_1)} & I^{(2\_1)} & I^{(3\_1)} & I^{(4\_1)} \\ I^{(1\_2)} & I^{(2\_2)} & I^{(3\_2)} & I^{(4\_2)} \\ I^{(1\_3)} & I^{(2\_3)} & I^{(3\_3)} & I^{(4\_3)} \\ I^{(1\_4)} & I^{(2\_4)} & I^{(3\_4)} & I^{(4\_4)} \end{pmatrix} = M_A \cdot M_{OUT} \quad (2)$$

If $$M_G = [S_G^{(1)}, S_G^{(2)}, S_G^{(3)}, S_G^{(4)}],$$

then M is computed by means of:

$$M = (M_{SCN}^{(2)})^{-1} \cdot M_{OUT} \cdot (M_G)^{-1} \cdot (M_{SCN}^{(1)})^{-1} \quad (3)$$

where $M_{OUT}$ is obtained by inversion of equation (2).

The system in FIG. 6 (an example of a measurement of transmitted light) is calibrated by taking a measurement in the incoming pathway. This will give the Mueller matrix, $$M_{SCN}^{(1)},$$

of the instrument in the incoming direction. A matrix of 16 intensity values results from intensity measurements with the generator's rotating ¼ wave plate in each of four positions −45 degrees, 0 degrees, 30 degrees and 60 degrees, while the analyzer's ¼ wave plate is placed in each of the same four positions.

Sixteen (16) gray scale images are taken with the object in place for each of the four generator states (¼ wave plate QWP1 at 45, 0, 30 and 60 degrees) combined with each of the same four analyzer states (¼ wave plate QWP2 set at 45, 0, 30 and 60 degrees while QWP1 is in each of its fours states). The generator produces polarized light at a particular orientation, set by a linear polarizer P1 and the QWP1 and. The analyser composed of QWP2 and the linear polarizer P2 turns light of a particular polarization into linearly polarized light.

The 16 grey scale values for each pixel are placed into a spatially resolved matrix, $I^{(mn)}$ which is the first element of the Stokes vector, $$S_D^{(mn)}$$

reaching the photodetector.

For every Stokes vector $$S_G^{(m)} \ (m = 1, 2, 3, 4)$$

produced by the generator, the intensity reaching the detector for each point of the sample ($I^{(mn)}$), is the first element of the Stokes vector $$S_D^{(mn)} \ (n = 1, 2, 3, 4)$$

given by:

$$S_D^{(mn)} = \overline{M}_A^{(n)} \cdot M \cdot M_{SCN}^{(1)} \cdot S_G^{(m)} \quad (4)$$

where $M=M_{ij}$ (i, j=0, 1, 2, 3) is the Mueller matrix of the sample under study, $$\overline{M}_A^{(n)}$$

is one of the four Mueller matrices of the analyzer unit (each corresponding to an independent state), and $$M_{SCN}^{(1)}$$

is the Mueller matrices of the experimental system itself (lenses, scanning unit and beam splitter), previously measured in the calibration process. For each generator-analyzer combination, the image is spatially resolved, giving a spatially resolved M. Let $M_A$ be the 4×4 auxiliary matrix with each row being the first row of every $$\overline{M}_A^{(n)} \text{ and } M_{OUT} = [S_{OUT}^{(1)}, S_{OUT}^{(2)}, S_{OUT}^{(3)}, S_{OUT}^{(4)}]$$

be another auxiliary matrix with $$S_{OUT}^{(m)}$$

each Stokes vector going into the analyzer unit. These matrices are then related by equation 2: If $$M_G = [S_G^{(1)}, S_G^{(2)}, S_G^{(3)}, S_G^{(4)}],$$

then M is computed by means of:

$$M = M_{OUT} \cdot (M_G)^{-1} \cdot (M_{SCN}^{(1)})^{-1} \quad (5)$$

where $M_{OUT}$ is obtained by inversion of equation (2).

From the spatially resolved Mueller matrix calculated for the apparatus in either FIG. 1 or in FIG. 6, images of the sample $I^{(OUT)}$ for any in-coming polarization state $S_{IN}$ can be obtained by:

$$\begin{pmatrix} I^{(OUT)} \\ S_1^{(OUT)} \\ S_2^{(OUT)} \\ S_3^{(OUT)} \end{pmatrix} = \begin{pmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{pmatrix} \cdot \begin{pmatrix} 1 \\ \cos(2\chi) \cdot \cos(2\varphi) \\ \sin(2\chi) \cdot \cos(2\varphi) \\ \sin(2\varphi) \end{pmatrix} = M \cdot S_{IN} \quad (6)$$

where $\chi$ and $\varphi$ represent, respectively, the azimuth and ellipticity of the incident Stokes vector on the Poincaré sphere[16]. Using equation 6, we can determine the Stokes vectors that produce images with both best and worst quality. This quality is defined below. This equation gives all output polarization properties. Here we consider only the image intensity, $I^{(OUT)}$, to which only the four elements of the first row of the Mueller matrix contribute.

One parameter that may be used to characterize image quality is the speckle noise (SN) or the inverse of the signal-to-noise ratio (SNR) (often used to describe speckle[17]) defined as the ratio between the standard deviation and the mean intensity across the whole image:

$$SN = (SNR)^{-1} = \frac{stdv(I^{(out)})}{mean(I^{(out)})} \quad (7)$$

Other measures of image quality are possible including contrast across a local feature of the image, the size of the smallest features resolved in the image, or measures which are combinations of SN, contrast and resolution including Fisher's linear discriminant.

The detailed steps followed to obtain improved images according to the present invention using the preferred Mueller matrix methodology are as follows. First the methodology for reflection images is given.

1) Calibrate system 10 in FIG. 1 by taking a measurement in the incoming pathway. This will give the Mueller matrix, $$M_{SCN}^{(1)},$$

of the instrument in the incoming direction. For this measurement the analyzer is moved to the usual position of a sample. An intensity detector is placed behind the analyzer. Any scanning optics are turned off. A matrix of 16 intensity values results from intensity measurements with the generator's rotating ¼ wave plate in each of four positions −45 degrees, 0 degrees, 30 degrees and 60 degrees, while the analyzer's ¼ wave plate is placed in each of the same four positions.

2) Continue calibration. A mirror is placed at the plane of the sample. The analyzer and the intensity detector are moved behind the last optical element of the system. This will give the Mueller matrix, $$M_{SCN}^{(2)},$$

of the instrument in the outgoing direction. Any scanning optics are turned off. A matrix of 16 intensity values results from intensity measurements with the generator's ¼ wave plate in each of four positions −45 degrees, 0 degrees, 30 degrees and 60 degrees, while the analyzer's ¼ wave plate is placed in each of the same four positions.

3) Take the intensity detector out of the system and turn the scanners on. Record the 16 gray scale images with the object in place for each of the four generator states (¼ wave plate at 45, 0, 30 and 60 degrees) combined with each of the 4 analyzer states (¼ wave plate at 45, 0, 30 and 60 degrees). The 16 grey scale values for each pixel are placed into a spatially resolved matrix, $I^{(mn)}$ which is the first element of the Stokes vector, $$S_D^{(mn)}$$

reaching the photodetector.

4) From $I^{(mn)}$ calculate $M_{out}$ from equation 2.
5) From equation 3, calculate M, the spatially resolved Mueller matrix of the object.
6) Choose values of the incident Stokes vector, $S_{IN}$, around the Poincaré sphere in predetermined increments of $\chi$ and $\varphi$ which represent, respectively, the azimuth and ellipticity of the incident Stokes vector on the Poincaré sphere[16]. Applying equation 6, reconstruct images, $I^{(out)}$, pixel by pixel for each incident Stokes vector.

7) For each image, calculate the image quality measure of choice, for example SNR as defined in equation 7.

8) Display the image with best quality.

It is noted that the calibration in 1) and 2) just above may reduce the effect of the instrument on the final polarization properties of the image. However, it is possible to perform the method without calibration. In this case, the steps following b) are identical. The Mueller matrix derived is the matrix corresponding to the object plus the instrument. When taking images in depth, a more complex calibration process may be undertaken. Beginning at the top of a sample, the Mueller matrix corresponding to a small thickness may be calculated. The calibration matrix $$M_{SCN}^{(1)}$$

for the next layer below becomes $$M_{LAYER1} \cdot M_{SCN}^{(1)}$$

and $$M_{SCN}^{(2)}$$

becomes $$M_{SCN}^{(2)} \cdot M_{LAYER1}.$$

The Mueller matrix of the current layer $M_{LAYER2}$ is then calculated as previously described. This method can be followed for all subsequent layers, incorporating the Mueller matrices for all layers above the one currently being measured into the calibration matrices.

Figure 2:
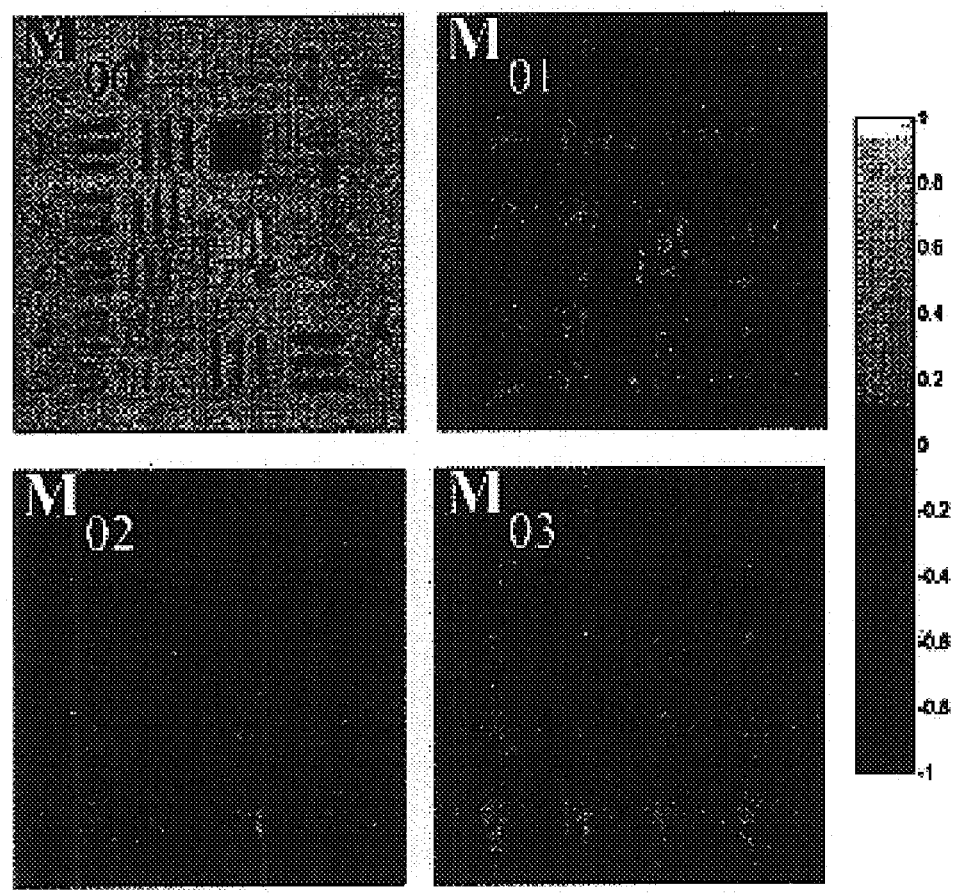
FIG. 2 shows elements of the first row of the spatially resolved Mueller matrix for a U.S.A.F. chart (4.4 mm square)
Figure 3:
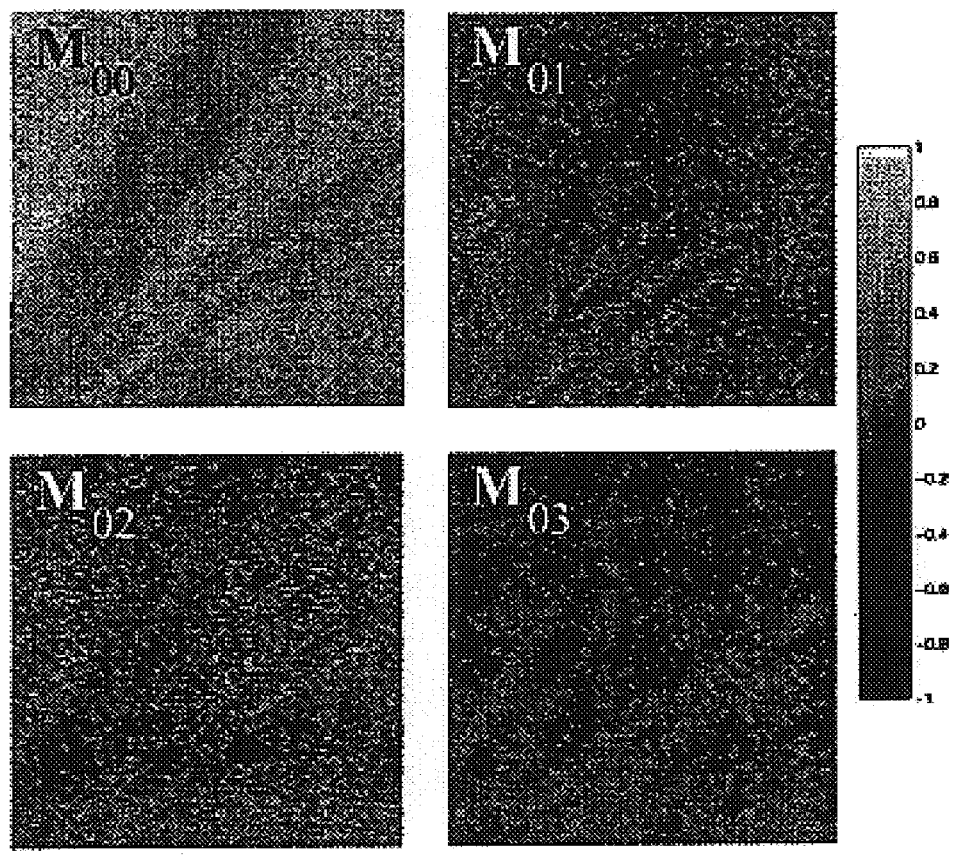
FIG. 3 shows elements of the first row of the spatially resolved Mueller matrix for a retinal region (2 degrees) for one sample subject's fundus, with the gray level code being shown at the right.

When system 10 is operated in microscope mode, spatially resolved Mueller matrices were calculated for two different samples: a U.S.A.F. resolution chart (primarily specular reflections) and a grey scale image on white paper (primarily diffuse reflections, not shown here). FIG. 2a shows the spatially resolved elements of the first row for the Mueller matrix corresponding to the USAF target. The averaged degrees of polarization were 0.87 (nearly specular) and 0.18 (highly depolarizing) for this target and the diffuse reflection respectively. In the ophthalmoscope mode we applied the procedure to retinal images recorded in a living human eye. In FIG. 3 we show the first row of the Mueller matrix for a retinal fundus region (with blood vessels).

Using these matrices, images were reconstructed for incident light with Stokes vectors with increments of 1 degree for azimuth and ellipticity over the Poincaré sphere. Images were obtained for incoming polarization states that could not be generated in an experimental system. For each matrix, both the best and the worst images were reconstructed using SNR as the measure of quality and the associated Stokes vectors calculated. The higher SNR shows that the best image calculated is better than the best measured with or without the polarizer in place.

Figure 4:
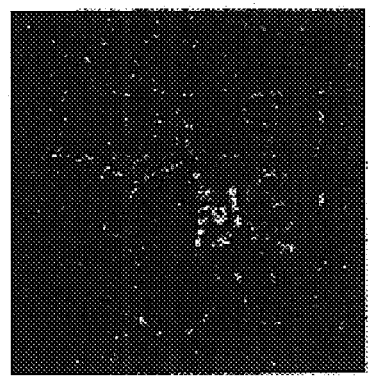
FIG. 4 shows results for the target in FIG. 2.
Figure 4:
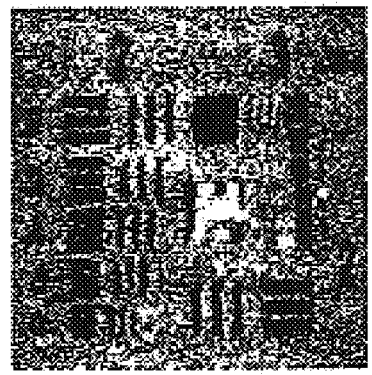
Figure 4:
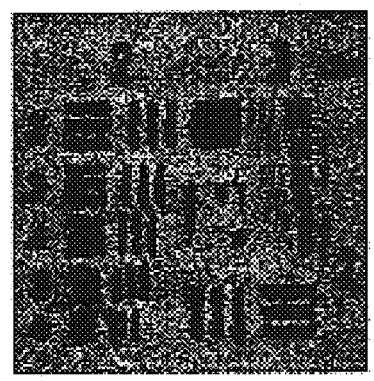
Figure 5:
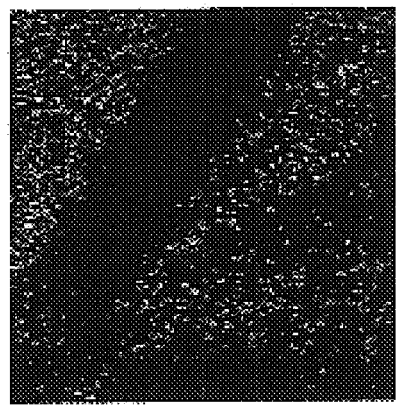
FIG. 5(a) shows the worst reconstructed image.
FIG. 5(b) shows the best original images.
FIG. 5(c) shows the best reconstructed images for the fundus image in FIG. 2 and an second sample subject (a 3 degree field)
Figure 5:
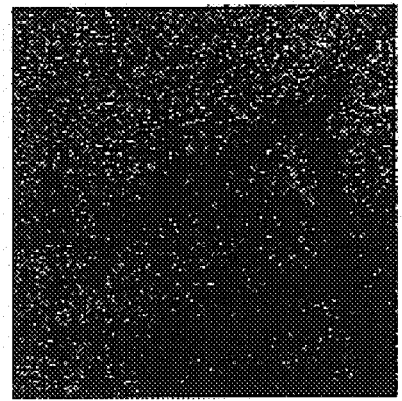
Figure 5:
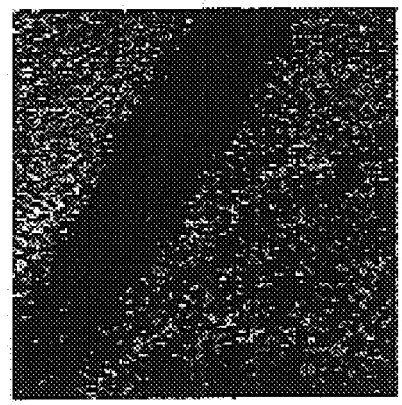
Figure 5:
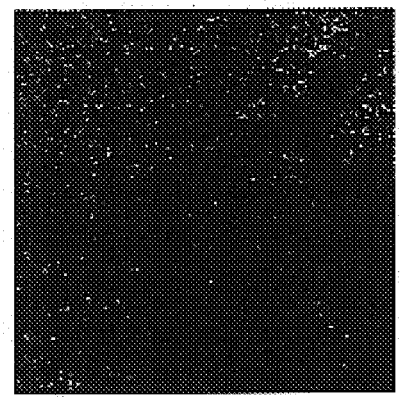
Figure 5:
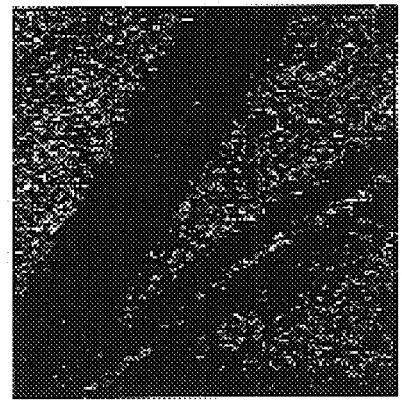
Figure 5:
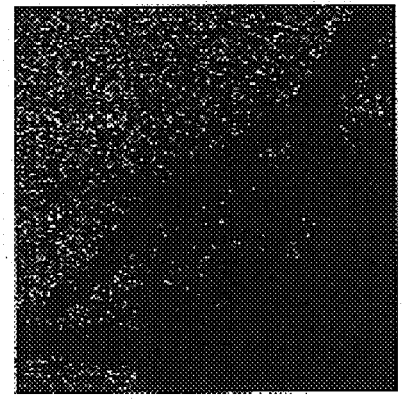

FIG. 4 shows the results obtained for the specular reflection in microscope mode. The best (c) and the worst reconstructed images (a) as well as one of the original images are shown (b). Results for the retinal fundus image of FIG. 3 are presented on the left in FIG. 5. On the right in FIG. 5 results for the retinal image of a second subject are shown. The original images presented are the best (lowest speckle noise or highest signal-to-noise ratio) of the images experimentally recorded (b). The worst reconstructed images are shown in (a). The improvement in the images obtained using this method was noticeable in all cases. Lower noise as well as higher contrast across features and higher resolution are seen in the best reconstructed image (c). Resolution improvement is demonstrated by the fact that more structural details and small features which are not discernible in the original images can be also observed. The improvement seen is better than that for frame averaging. Differences in the signal to noise as defined in equation 7 between the original and the best images were 48% for the specular target (70% for the diffuse target) in microscope mode and 45% for the retinal fundus image of FIG. 4. The Stokes vectors for the best specular image in FIG. 4 was $[1, -0.565, -0.099, -0.819]^T$ ($[1, 0.220, 0.604, -0.766]^T$ for the diffuse reflection) and those corresponding to the optimal retinal image were $[1, 0.719, 0.262, 0.643]^T$ for a subject measured in FIG. 3 and $[1, -0.969, 0.171, 0.174]^T$ for the second subject with results in FIG. 5. Moreover, an increase of up to 30% was found in the contrast across the blood vessels of the subjects presented here.

Improvements in image quality using the present invention have been obtained for two different confocal scanning laser imaging systems, both indicated in FIG. 1. These include a confocal scanning laser microscope and a confocal scanning laser ophthalmoscope (where the optics of the eye is the final imaging element before the object of interest (the fundus)). Improvements are obtained whether or not a confocal pinhole 26 is used in front of the hotodetector and regardless of what size of confocal pinhole is used. Improvements are also obtained for any wavelength used.

Thus, it will be appreciated by those skilled in the art that the confocal imaging system shown in FIG. 1 is meant to be a non-limiting example of an apparatus constructed in accordance with the present invention. The confocal imaging system shown in FIG. 1 is one that has pinhole 26 conjugate to the object plane of interest so that apparatus 10 excludes light reflected from the object which is not in-focus on the detector 22. This leads to improved contrast because of the exclusion of scattered light in addition to the ability to resolve structures in depth and to reconstruct three-dimensional images is enhanced. If depth resolution is important, then system 10 preferably should be used with confocal pinhole 26. However, scanning laser ophthalmoscopy and microscopy is performed with a larger pinhole in place of the confocal pinhole or with other specialty apertures or without a pinhole and the present invention may be implement using an apparatus absent the confocal pinhole using the methodology described herein which also gives improved image quality.

Similarly, the light source may be an incoherent light source or it may be a laser producing coherent light beams as light beams with the different polarization states can be produced. Diode lasers producing partially coherent light beams may also be used. Also, instead of using the fixed linear polarizer P1 in the generator 12 in apparatus 10 of FIG. 1, a light source with intrinsic linear polarization may be used.

In this description, scanning the beam illuminating the object which is then descanned allows a point detector to be used and the image to be recreated pixel by pixel using timing signals. If the beam is scanned and the light transmitted by an object is recorded, a stationary single detector cannot be used. In this situation, a moving single detector or moving linear array synchronized to the scanning beam or an area array of detectors with an exposure equivalent to 1 frame of the scan (e.g. a CCD array) may be used to record the image. An area of the object may be illuminated with a scanning beam and reflected images without descanning could be recorded using a moving single detector or a moving linear array of detectors synchronized to the scanning beam or an area array of detectors with an exposure equivalent to 1 frame of the scan (eg a CCD array) could be used to record the image. If a stationary beam were used to illuminate the object, any detector which allowed spatial resolution of the image could be used including a single moving detector, a moving linear array of detectors or an area array of detectors (e.g. a CCD array). The pixelated image that results from any of the above configurations could then be analyzed as described herein.

Secondly the methodology for transmission images is given.

1) Calibrate system in FIG. 6 by taking a measurement in the incoming pathway. This will give the Mueller matrix, $$M_{SCN}^{(1)},$$

of the instrument in the incoming direction. For this the sample is removed. The intensity detector is behind the analyzer. Any scanning optics are turned off. A matrix of 16 intensity values results from intensity measurements with the generator's rotating ¼ wave plate in each of four positions −45 degrees, 0 degrees, 30 degrees and 60 degrees, while the analyzer's ¼ wave plate is placed in each of the same four positions.

2) tIf using a supplementary detector for calibration, remove it. Turn the scanners (if any) on. Record the 16 gray scale images with the object in place for each of the four generator states (¼ wave plate at 45, 0, 30 and 60 degrees) combined with each of the 4 analyzer states (¼ wave plate at 45, 0, 30 and 60 degrees). The 16 grey scale values for each pixel are placed into a spatially resolved matrix, $I^{(mn)}$ which is the first element of the Stokes vector, $$S_D^{(mn)}$$

reaching the photodetector.

3) From $I^{(mn)}$ calculate $M_{out}$ from equation 2.

4) From equation 5, calculate M, the spatially resolved Mueller matrix of the object.

5) Choose values of the incident Stokes vector, $S_{IN}$, around the Poincaré sphere in predetermined increments of $\chi$ and $\phi$ which represent, respectively, the azimuth and ellipticity of the incident Stokes vector on the Poincaré sphere[16]. Applying equation 6, reconstruct images, $I^{(out)}$, pixel by pixel for each incident Stokes vector.

6) For each image, calculate the image quality measure of choice, for example SNR as defined in equation 7.

7) Display the image with best quality.

It is noted that the calibration in 1) just above may reduce the effect of the instrument on the final polarization properties of the image. However, it is possible to perform the method without calibration. In this case, the steps following 1) are identical. The Mueller matrix derived is the matrix corresponding to the object plus the instrument following b) are identical. The Mueller matrix derived is the matrix corresponding to the object plus the instrument.

Figure 7:
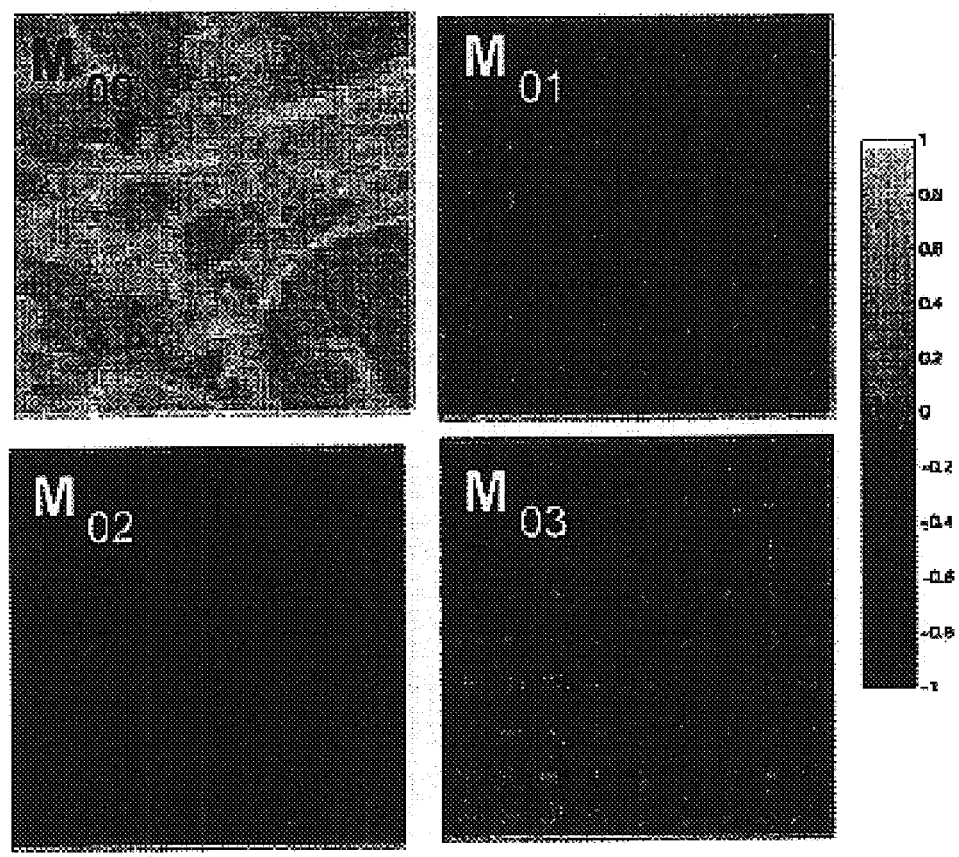
FIG. 7 shows elements of the first row of the spatially resolved Mueller matrix for a tissue sample measured in the modified Macroscope.

When the system in FIG. 6 is operated in transmission mode, spatially resolved Mueller matrices were calculated for a tissue sample. FIG. 7 shows the spatially resolved elements of the first row for the Mueller matrix corresponding to the tissue target.

Using this matrix, images were reconstructed for incident light with Stokes vectors with increments of 1 degree for azimuth and ellipticity over the Poincaré sphere. Images were obtained for incoming polarization states that could not be generated in an experimental system. For each matrix, both the best and the worst images were reconstructed using best SNR and best contrast as the measures of quality and the associated Stokes vectors calculated. The highest SNR measure shows improvement of some features and the highest contrast shows improvement of other figures.

Figure 8:
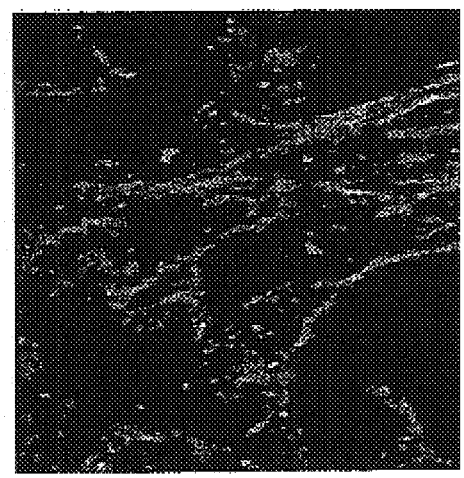
FIGS. 8(a), (b) and (c) show results for the sample in FIG. 7.
FIG. 8(b) shows the best reconstructed image with maximum contrast.
FIG. 8(c) shows the best reconstructed image with maximum signal to noise ratio.
Figure 8:
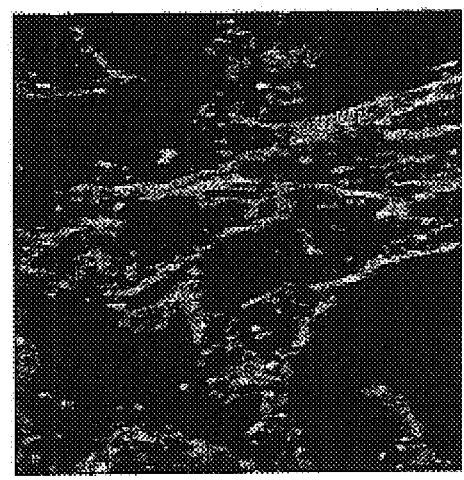
Figure 8:
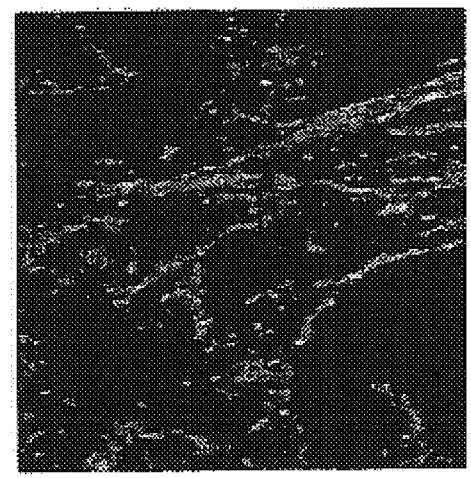

FIG. 8 shows the best (b) reconstructed image using contrast as the quality measure, as well as the best reconstructed image (c) using the best SNR (highest signal-to-noise ratio) as the quality measure as well as the best original image (a). The original image presented is an image experimentally recorded (a). The improvement in the images obtained using this method was noticeable in all cases.

Improvements in image quality using the present invention have been obtained for three different confocal scanning laser imaging systems, indicated in FIGS. 1 and 6. These include a confocal scanning laser microscope, a confocal scanning laser ophthalmoscope (where the optics of the eye is the final imaging element before the object of interest (the fundus)) and a Macroscope. Improvements are obtained in reflection and transmission modes, whether or not a confocal pinhole 26 is used in front of the hotodetector and regardless of what size of confocal pinhole is used. Improvements are also obtained for any wavelength used.

Thus, it will be appreciated by those skilled in the art that the confocal imaging system shown in FIG. 1 and the nonconfocal system in FIG. 6 (one measuring reflected light and the other transmitted light) are meant to be a non-limiting examples of an apparatus constructed in accordance with the present invention. The confocal imaging system shown in FIG. 1 is one that has pinhole 26 conjugate to the object plane of interest so that apparatus 10 excludes light reflected from the object which is not in-focus on the detector 22. This leads to improved contrast because of the exclusion of scattered light in addition to the ability to resolve structures in depth and to reconstruct three-dimensional images is enhanced. If depth resolution is important, then system 10 preferably should be used with confocal pinhole 26. However, scanning laser ophthalmoscopy and microscopy is performed with a larger pinhole in place of the confocal pinhole or with other specialty apertures or without a pinhole and the present invention may be implement using an apparatus absent the confocal pinhole using the methodology described herein which also gives improved image quality. This instrument could also be combined with an optical coherent tomography measurement or could be an optical coherent tomography instrument.

Similarly, the light source in FIG. 1 or FIG. 6 may be an incoherent light source or it may be a laser producing coherent light beams as light beams with the different polarization states can be produced. Diode lasers producing partially coherent light beams may also be used. Also, instead of using the fixed linear polarizer P1 in the generator 12 in apparatus 10 of FIG. 1 or in FIG. 6, a light source with intrinsic linear polarization may be used.

In the description in FIG. 1, scanning the beam illuminating the object which is then descanned allows a point detector to be used and the image to be recreated pixel by pixel using timing signals. In FIG. 6, the laser beam is scanned in one direction and the stage is scanned in the perpendicular direction and a detector with an array of light sensitive elements is used. If the beam is scanned and the light transmitted by an object is recorded, a stationary single detector cannot be used. In this situation, a moving single detector or moving linear array synchronized to the scanning beam or an area array of detectors with an exposure equivalent to 1 frame of the scan (e.g. a CCD array as in FIG. 6) may be used to record the image. An area of the object may be illuminated with a scanning beam and reflected images without descanning could be recorded using a moving single detector or a moving linear array of detectors synchronized to the scanning beam or an area array of detectors with an exposure equivalent to 1 frame of the scan (eg a CCD array) could be used to record the image. If a stationary beam were used to illuminate the object, any detector which allowed spatial resolution of the image could be used including a single moving detector, a moving linear array of detectors or an area array of detectors (e.g. a CCD array). In any of the above descriptions, the object stage may be scanned and this would replace the scanning of the light beam. The pixelated image that results from any of the above configurations could then be analyzed as described herein.

Although in the invention disclosed herein the inventors have calculated the 16 elements of the Mueller matrix, just 4 of them (first row) are used to calculate the final improved image. Therefore, an additional methodology based on the calculation of just these 4 elements instead of 16 may result in the same improved images.

Therefore, for each independent polarization state emerging from the generator unit $$S_G^{(i)}(i=1,2,3,4),$$

the Stokes vector associated with the light reaching the recording state, $S_F^{(i)}$, when no analizer is included in the system is given by:

$$S_F^{(i)} = M_T \cdot S_G^{(i)} = M_{SYST}^{(2)} \cdot M \cdot M_{SYST}^{(1)} \cdot S_G^{(i)} \qquad (1b)$$

or when transmitted light is measured $$S_F^{(i)} = M_T \cdot S_G^{(i)} = M \cdot M_{SYST}^{(1)} \cdot S_G^{(i)} \qquad (4b)$$

where $$M_T = m_{lk}^{(T)} \quad (l, m = 0, 1, 2, 3),$$

is the Mueller matrix of the complete system and M is the Mueller matrix of the sample under study.

$$M_{SYST}^{(1)} \text{ and } M_{SYST}^{(2)}$$

are the Mueller matrices obtained from the calibration procedure.

Let $M_0$ be the 4×1 column vector which elements are the first row of the Mueller matrix $M_T$ in a transposed position.

When four independent polarization states, $$S_G^{(i)}(i=1,2,3,4)$$

are incident, then it is verified:

$$I_F = \begin{pmatrix} I_1 \\ I_2 \\ I_3 \\ I_4 \end{pmatrix} = \begin{pmatrix} S_{0G}^{(1)} & S_{1G}^{(1)} & S_{2G}^{(1)} & S_{3G}^{(1)} \\ S_{0G}^{(2)} & S_{1G}^{(2)} & S_{2G}^{(2)} & S_{3G}^{(2)} \\ S_{0G}^{(3)} & S_{1G}^{(3)} & S_{2G}^{(3)} & S_{3G}^{(3)} \\ S_{0G}^{(4)} & S_{1G}^{(4)} & S_{2G}^{(4)} & S_{3G}^{(4)} \end{pmatrix} \cdot \begin{pmatrix} m_{00}^{(T)} \\ m_{01}^{(T)} \\ m_{02}^{(T)} \\ m_{03}^{(T)} \end{pmatrix} = \begin{pmatrix} (S_G^{(1)})^T \\ (S_G^{(2)})^T \\ (S_G^{(3)})^T \\ (S_G^{(4)})^T \end{pmatrix} \cdot \begin{pmatrix} m_{00}^{(T)} \\ m_{01}^{(T)} \\ m_{02}^{(T)} \\ m_{03}^{(T)} \end{pmatrix} = M_G \cdot M_0 \qquad (2b)$$

where $I_i$ (i=1, 2, 3, 4) corresponds to the recorded images for each independent polarization states $$S_G^{(i)}.$$

Finally $M_0$ is obtained by inversion of equation (2b):

$$M_0 = (M_G)^{-1} \cdot I_F \qquad (3b)$$

From the spatially resolved vector $M_0$, images of the sample $I_{out}$ for any in-coming polarization state $S_{IN}$ can be obtained by:

$$I_{FINAL} = \qquad (6b)$$

$$(m_{00}^{(T)} \quad m_{01}^{(T)} \quad m_{02}^{(T)} \quad m_{03}^{(T)}) \cdot \begin{pmatrix} 1 \\ \cos(2\chi) \cdot \cos(2\varphi) \\ \sin(2\chi) \cdot \cos(2\varphi) \\ \sin(2\varphi) \end{pmatrix} = M_0^T \cdot S_{IN}$$

where $\chi$ and $\phi$ represent, respectively, the azimuth and ellipticity of the incident Stokes vector on the Poincaré sphere and $M_0^T$ is the transposed vector of $M_0$. Using equation 6b, we can determine the Stokes vectors that produce images with both best and worst quality using the chosen measure of image quality.

The detailed steps followed to obtain improved images according to the present invention using apparatus 10 in FIG. 1 are as follows. The optical scanning system (shown in FIG. 10) is calibrated as described above a) calibrating the confocal scanning laser system (microscope or ophthalmoscope) modified to include a polarization generator and a polarization analyzer to obtain a Mueller matrix $$M_{SCN}^{(1)},$$

of the instrument in the incoming direction, wherein a matrix of 16 intensity values results from intensity measurements with a fixed linear polarizer and a rotating ¼ wave plate located in said generator positioned in each of four positions including −45 degrees, 0 degrees, 30 degrees and 60 degrees, while a fixed linear polarizer and a ¼ wave plate (symmetric configuration with respect to the generator) located in the analyzer is placed in each of the same four positions; in order to measure the above cited matrix, the analyzer and an intensity detector are placed in the place of the sample;

b) calibrating the confocal scanning instrument to obtain a Mueller matrix $$M_{SCN}^{(2)},$$

of the instrument in the outgoing direction, wherein a matrix of 16 intensity values results from intensity measurements with a fixed linear polarizer and a rotating ¼ wave plate located in said generator positioned in each of four positions including −45 degrees, 0 degrees, 30 degrees and 60 degrees, while a fixed linear polarizer and a ¼ wave plate (symmetric configuration with respect to said generator) located in said analyzer is placed in each of the same four positions; in this case a mirror is placed in place of the sample and the analyzer unit and the intensity detector are placed in the confocal detection arm;

c) analyzer and detector are removed from the recording pathway and just the generator is used for the new method.

d) placing the object in the confocal scanning apparatus and focusing light onto the object and recording four gray scale images with the object in place for each of four generator states with a ¼ wave plate at 45, 0, 30 and 60 degrees;

e) placing the four grey scale values for each pixel into a spatially resolved vector, $I_F$, which elements are the first element of the four $S_F^{(i)}$ reaching the photodetector;

f) from equation 3b calculate $M_0$, the spatially resolved auxiliary which elements are the first row of the total Mueller matrix, $M_T$;

g) choosing values of an incident Stokes vector, $S_{IN}$, around a Poincaré sphere in predetermined increments of $\chi$ and $\phi$ which represent, respectively, the azimuth and ellipticity of the incident Stokes vector on the Poincaré sphere;

h) applying equation 4b to reconstruct images, $I_{OUT}$, pixel by pixel for each incident Stokes vector;

i) for each image, calculate the image quality measure of choice; and j) display the image with best value of the image quality measure.

It is noted that the calibration in a) and b) just above may reduce the effect of the instrument on the final polarization properties of the image. However, it is possible to perform the method without calibration. In this case, the steps following b) are identical. The first row derived is the first row of the Mueller matrix of the object +instrument).

The detailed steps followed to obtain improved images according to the present invention using the apparatus in FIG. 6 are as follows. The optical scanning system (shown in FIG. 6) is calibrated as described above a) calibrating the Macroscope modified to include a polarization generator and a polarization analyzer to obtain a Mueller matrix $$M_{SCN}^{(1)},$$

of the instrument in the incoming direction, wherein a matrix of 16 intensity values results from intensity measurements with a fixed linear polarizer and a rotating ¼ wave plate located in said generator positioned in each of four positions including −45 degrees, 0 degrees, 30 degrees and 60 degrees, while a fixed linear polarizer and a ¼ wave plate (symmetric configuration with respect to the generator) located in the analyzer is placed in each of the same four positions; in order to measure the above cited matrix, the analyzer is placed in the place of the sample;

b) analyzer is removed from the recording pathway and just the generator is used for the new method.

c) placing the object in the Macroscope and focusing light onto the object and recording four gray scale images with the object in place for each of four generator states with a ¼ wave plate at 45, 0, 30 and 60 degrees;

e) placing the four grey scale values for each pixel into a spatially resolved vector, $I_F$, which elements are the first element of the four $$S_F^{(i)}$$

reaching the photodetector;

$$S_F^{(i)} = M_T \cdot S_G^{(i)} = M \cdot M_{SYST}^{(1)} \cdot S_G^{(i)} \quad (1c)$$

f) from equation 3b calculate $M_0$, the spatially resolved auxiliary which elements are the first row of the total Mueller matrix, $M_T$;

g) choosing values of an incident Stokes vector, $S_{IN}$, around a Poincaré sphere in predetermined increments of $\chi$ and $\phi$ which represent, respectively, the azimuth and ellipticity of the incident Stokes vector on the Poincaré sphere;

h) applying equation 4b to reconstruct images, $I_{OUT}$, pixel by pixel for each incident Stokes vector;

i) for each image, calculate the image quality measure of choice; and j) display the image with best value of the image quality measure.

In situations where the state of polarization of the input beam cannot be controlled (e.g. astronomical observations), or in situations where the output illumination is intrinsic to the sample (e.g. fluorescence microscopy), this shortened method just described may be modified to use a single input polarization state and to sample the spatially resolved image for 4 output polarization states. The 4 elements of the Stokes vector associated with uncontrolled light, $S_{IN}$ can be calculated from equations 2, where the matrix on the left containing the intensities now is a column vector 4×1 and the matrix $M_{OUT}$ is the unknown Stokes vector, $S_{IN}$. This is shown in equation 1d $$(M_A)^{-1} \cdot \begin{pmatrix} I^{(1)} \\ I^{(2)} \\ I^{(3)} \\ I^{(4)} \end{pmatrix} = (M_A)^{-1} \cdot I_F = S_{IN} \quad (1d)$$

Images corresponding to any output polarization state, $$I_\alpha^{OUT},$$

are then obtained from equation 2c as:

$$\begin{pmatrix} I_\alpha^{(OUT)} \\ S_{1\alpha}^{(OUT)} \\ S_{2\alpha}^{(OUT)} \\ S_{3\alpha}^{(OUT)} \end{pmatrix} = \overline{M}_A^\alpha \cdot S_{IN} \quad (2c)$$

where $\overline{M}_A^\alpha$ is the Mueller matrix for each theoretical orientation of the fast axis of the ¼ wave plate of the analyzer unit.

The detailed methodology is as follows:

a) generator and detector are removed from the recording pathway and just the analyzer is used for this method;

b) passing the light coming from the object trough the analyzer unit.

c) recording one gray scale image for each of four analyser states with a ¼ wave plate at 45, 0, 30 and 60 degrees;

e) placing said four grey scale values for each pixel into a spatially resolved vector, $I_F$, which elements are the first element of the four Stokes vectors reaching the photodetector;

f) from equation 1d calculate $S_{IN}$, the spatially resolved Stokes vector corresponding to the sample light beam;

g) predetermined increments for the orientation of the fast axis of the ¼ wave plate of the analyzer unit, $\alpha$;

h) applying equation 2c to reconstruct images, $$I_\alpha^{(OUT)},$$

pixel by pixel for each orientation if the ¼ wave plate;

i) for each image, calculate the image quality measure of choice; and j) display the image with best value of the image quality measure.

It will be understood that the present methodology is not restricted to the calculation of 4×4 Mueller matrices from combinations of 4 incoming and 4 outgoing polarization states in the first method discussed above or to the first row of the Mueller matrix in the second method or to one input and four output beams in the third method disclosed above. It is noted that any other matrix which describes the effect of the object on the polarization properties of light may also be used. Thus, while Mueller matrices are always 4×4 it is possible to use more combinations of beam in- and beam out-polarization states.

When Mueller matrices are used, once the spatially resolved 4×4 Mueller matrix of the object is constructed from the detected light signals one constructs spatially resolved images of the object for a set of theoretical polarization states of the incident beam of light in addition to those input states actually generated in the incident light beams. The images are calculated point by point for a large number of polarization states (sampled all around the Poincare sphere in 1 degree steps in one example implementation). These polarization states can each be described by a Stokes vector where the Stokes vector characterizes the polarization of the input light beam. The first element of the vector gives the intensity of the beam, the second element gives the degree of vertical or horizontal polarization, the third element of the Stokes vector gives the degree of +45 or −45 linear polarization and the fourth element of the Stokes vector gives the degree and direction of circular polarization. So for each image constructed, one uses the Mueller matrix which has been calculated point by point and a Stokes vector to generate an image point by point. Once the calculation has been done for a chosen number of polarization states, then the best image is chosen. The calculation would normally include four independent polarization states that the generator unit is designed to produce as well as a set of theoretical input polarization states that are not easily produced experimentally.

In conclusion, the present invention demonstrates the use of Mueller-matrix polarimetry for improving the quality of confocal scanning microscopy, confocal scanning ophthalmoscopy and optical coherence tomography images. In another embodiment of the invention the optical system may use fast electro-optical modulators such as liquid-crystal variable retarders or photo-elastic modulators. The polarization state which gives the best improvement in image quality differs for the specular and diffuse reflections in microscope mode and for the two analyzed subjects in ophthalmoscopic mode. In general as in imaging with polarized light[18], the Stokes vector corresponding to the best image may vary with the characteristics of the object being measured. To implement the technique, the improvement in the image may be rapidly calculated and displayed in software. The best image may be calculated with respect to a region of the image of interest. An implementation of this technique in commercially available microscopy, macroscopy, optical coherence tomography and ophthalmologic instruments[10,19] or in a specialized instrument enhances fundus imaging and improves diagnosis techniques.

As used herein, the terms "comprises" and "comprising" are to be construed as being inclusive and open ended, and not exclusive. Specifically, when used in this specification including claims, the terms "comprises" and "comprising" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. J. B. Pawley (Editor), Handbook of Biological Confocal Microscopy, $2^{nd}$ ed. Plenum, New York (1995).
2. A. C. Ribes, S. Damaskinos, A. E. Dixon, K. A. Kellis, S. P. Duttagupta, and P. M. Fauchet, Progress in Surface Science, 50, 295 (1995).
3. R. H. Webb, G. W. Hughes, and F. C. Delori, Appl. Opt. 26, 1492 (1987).
4. J. Liang, D. R. Williams, and D. T. Miller, J. Opt. Soc. Am. A 14, 2884 (1997).
5. I. Iglesias and P. Artal. Opt. Lett. 25, 1804 (2000).
6. K. Muth, M. C. W. Campbell, A. J. Roorda, and C. Cui, OSA Technical Digest Series 1, 56–59 (1997).
7. M. P. Rowe, E. N. Pugh, Jr., J. S. Tyo, and N. Engheta, Opt. Lett. 20, 608 (1995).
8. Y. Gang and L. V. Wang, Opt. Lett. 24, 537 (1999).
9. S. Jiao Y. Gang and L. V. Wang, Appl. Opt. 39, 6318 (2000).
10. A. W. Dreher, K. Reiter, and R. N. Weinred, Appl. Opt. 31, 3730 (1992).
11. W. G. Egan, W. R. Johnson, and V. S. Whitehead, Appl. Opt. 30, 435 (1991)
12. W. Mickols, I Tinoco, J. E. Katz, M. F. Maestre, and C. Bustamente, Rev. Sci. Instrum. 12, 2228 (1985).
13. R. A. Chipman, in *Handbook of Optics,* 2nd ed., M. Bass, ed. (McGraw-Hill, New York, 1995) Sec. 22.1.
14. J. M. Bueno and J. Jaronski, Opthal. Physiol. Opt. 21, 384 (2001).
15. J. M. Bueno and P. Artal, Opt. Lett. 24, 64 (1999).
16. H. G. Jerrard, J. Opt. Soc. Am. 44, 634 (1954).
17. J. W. Goodman, in *Laser Speckle and Related Phenomena,* 2nd ed., J. C. Dainty, ed., Vol. 9 of Topics in Applied Physics (Springer-Verlag, 1984), 9–75.
18. J. M. Bueno and P. Artal, J. Opt. Soc. Am A 18, 489 (2001).
19. B. Pelz, C. Weschenmoser, S. Goelz, J. P. Fischer, R. O. W. Burk, and J. F. Bille, Proc. SPIE 2930, 92 (1996).

Therefore what is claimed is:

1. A method for producing images of an object or region of interest of the object, comprising the steps of:
   a) producing an incident beam of light in a pre-selected polarization state and scanning said incident earn of light point by point across an object or region of interest of the object;
   b) detecting light intensity signals corresponding to beams of light in a pre-selected number of polarization states reflected point by point from the object or region of interest of the object and storing electronic signals corresponding to the detected light intensity signals;
   c) repeating steps a) and b) for an effective number of pre-selected polarization states of the incident beam of light;
   d) constructing a spatially resolved matrix of the object point by point from the detected light intensity signals and from said spatially resolved matrix constructing spatially resolved images of the object or region of interest of the object for a set of theoretical polarization states of the incident beam of light in addition to those input states generated in the incident beam of light, said matrix being selected to describe the effect of the object on the polarization properties of light;
   e) characterizing image quality of each image in accordance with an effective image quality parameter and based upon said characterization selecting a best image of said object or region of said object; and
   f) visually displaying said best image.

2. The method according to claim 1 wherein the matrix is a 4×4 Mueller matrix, and wherein said effective number of pre-selected polarization states of the incident beam of light is four, and wherein said pre-selected number of polarization states in the pathway which records the reflected point by point signal from the object is four.

3. The method according to claim 1 wherein the effective image quality parameter is the signal-to-noise ratio.

4. The method according to claim 1 wherein the step of detecting an array of light signals reflected from the object or region of interest of the object includes detecting light reflected from multiple locations on the object or region of interest of the object point by point using a movable detector.

5. A method for producing images of an object or region of interest of the object, comprising the steps of:
   a) producing an incident beam of tight in a pre-selected polarization state and scanning said incident beam of light point by point across an object or region of interest of the object;
   b) detecting light intensity signals corresponding to beams of light reflected point by point from the object or region of interest of the object and storing electronic signals corresponding to the detected light intensity signals;
   c) repeating steps a) and b) for an effective number of pre-selected polarization states of the incident beam of light;
   d) constructing a spatially resolved vector of the object point by point from the detected light intensity signals and from said spatially resolved vector constructing spatially resolved images of the object or region of interest of the object for a set of theoretical polarization states of the incident beam of light in addition to those input states generated in the incident beam of light, said vector comprised of independent elements of a matrix being selected to describe the effect of the object on the polarization properties of light;
   e) characterizing image quality of each image in accordance with an effective image quality parameter and based upon said characterization selecting a best image of said object; and
   f) visually displaying said best image.

6. The method according to claim 5 wherein the vector is the first row of the matrix and the matrix is a 4×4 Mueller matrix, and wherein said effective number of pre-selected polarization states of the incident beam of light is four.

7. The method according to claim 5 wherein the effective image quality parameter is the signal-to-noise ratio.

8. The method according to claim 5 wherein the step of detecting light signals reflected from the object or region of interest of the object includes detecting light reflected from multiple locations on the object or region of interest of the object point by point using a movable detector.

9. A method for producing images of an object or region of interest of the object, comprising the steps of:
   a) producing an incident beam of light in a pre-selected polarization state and illuminating an object or region of interest of the object with the selectively polarized beam of light;
   b) detecting an array of light intensity signals reflected from spatially distinct points of the object or region of interest of the object and storing electronic signals corresponding to said detected array of light signals;
   c) repeating steps a) and b) for an effective number of pre-selected polarization states of the incident beam of light;
   d) constructing a spatially resolved vector comprised of independent elements of a spatially resolved matrix of the object point by point from the detected light intensity signals and from said spatially resolved vector constructing spatially resolved images of the object or region of interest of the object for a set of theoretical polarization states of the incident beam of light in addition to those input states generated in the incident beam of light, said matrix being selected to describe the effect of the object on the polarization properties of light;
   e) characterizing image quality of each image in accordance with an effective image quality parameter and based upon said characterization selecting a best image of said object; and
   f) visually displaying said best image.

10. The method according to claim 9 wherein the step of detecting an array of light signals reflected from the object or region of interest of the object includes simultaneously detecting light reflected from multiple locations on the object or region of interest of the object using an array detector.

11. The method according to claim 10 wherein the array detector is a charge coupled detector.

12. The method according to claim 9 wherein the step of detecting an array of light signals reflected from the object or region of interest of the object includes detecting light reflected from multiple locations on the object or region of interest of the object point by point using a movable detector.

13. The method according to claim 9 wherein the effective image quality parameter is signal-to-noise ratio.

14. A method for producing images of an object or region of interest of the object, comprising the steps of:
   a) producing an incident beam of light in a pre-selected polarization state and illuminating an object or region of interest of the object with the selectively polarized beam of light;

b) detecting an array of light intensity signals reflected from spatially distinct points of the object or region of interest of the object and storing electronic signals corresponding to said detected array of light signals;

c) repeating steps a) and b) for an effective number of pre-selected polarization states of the incident beam of light;

d) constructing a spatially resolved matrix of the object from the detected light intensity signals and from said spatially resolved matrix constructing spatially resolved images of the object or region of interest of the object for a set of theoretical polarization states of the incident beam of light in addition to those input states generated in the incident beam of light, said matrix being selected to describe the effect of the object on the polarization properties of light;

e) characterizing image quality of each image in accordance with an effective image quality parameter and based upon said characterization selecting a best image of said object; and f) visually displaying said bet image.

15. The method according to claim 14 wherein the step of detecting an array of light signals reflected from the object or region of interest of the object includes simultaneously detecting light reflected from multiple locations on the object or region of interest of the object using an array detector.

16. The method according to claim 15 wherein the array detector is a charge coupled detector.

17. The method according to claim 14 wherein the step of detecting an array of light signals reflected from the object or region of interest of the object includes detecting light reflected from multiple locations on the object or region of interest of the object point by point using a movable detector.

18. The method according to claim 14 wherein the effective image quality parameter is signal-to-noise ratio.

19. A method for producing images of an object using confocal scanning laser microscopy, comprising the steps of:

a) calibrating a confocal scanning laser microscope modified to include a polarization generator and a polarization analyzer to obtain a Mueller matrix $$M_{SCN}^{(1)},$$

of the instrument in the incoming direction, wherein a matrix of 16 intensity values results from intensity measurements with a rotating ¼ wave plate located in said generator positioned in each of four positions including 45 degrees, 0 degrees, 30 degrees and 60 degrees, while a ¼ wave plate located in said analyzer is placed in each of the same four positions;

b) calibrating said modified confocal scanning instrument to obtain a Mueller matrix $$M_{SCN}^{(2)},$$

of the instrument in the outgoing direction, wherein a matrix of 16 intensity values results from intensity measurements with a rotating ¼ wave plate located in said generator positioned in each of four positions including 45 degrees, 0 degrees, 30 degrees and 60 degrees, while a ¼ wave plate located in said analyzer is placed in each of the same four positions;

c) placing said object in said modified confocal scanning apparatus and focusing light onto said object and recording sixteen gray scale images with the object in place for each of four generator states with a ¼ wave plate at 45, 0, 30 and 60 degrees combined with each of the four analyzer states 1/4 wave plate at 45, 0, 30 and 60 degrees;

d) placing said sixteen grey scale values for each pixel into a spatially resolved matrix, $I^{(mn)}$, which is a first element of a Stokes vector, $$S_D^{(mn)}$$

reaching the photodetector;

e) from $I^{(mn)}$ calculate $M_{out}$ from equation 2, given by $$\begin{pmatrix} I^{(1\_1)} & I^{(2\_1)} & I^{(3\_1)} & I^{(4\_1)} \\ I^{(1\_2)} & I^{(2\_2)} & I^{(3\_2)} & I^{(4\_2)} \\ I^{(1\_3)} & I^{(2\_3)} & I^{(3\_3)} & I^{(4\_3)} \\ I^{(1\_4)} & I^{(2\_4)} & I^{(3\_4)} & I^{(4\_4)} \end{pmatrix} = M_A \cdot M_{OUT};$$

f) from equation 3, given by $$M = (M_{SCN}^{(2)})^{-1} \cdot M_{OUT} \cdot (M_G)^{-1} \cdot (M_{SCN}^{(1)})^{-1},$$

calculate M, the spatially resolved Mueller matrix of the object;

g) choosing values of an incident Stokes vector, $S_{IN}$, around a Poincaré sphere in predetermined increments of $\chi$ and $\phi$ which represent, respectively, the azimuth and ellipticity of the incident Stokes vector on the Poincaré sphere;

h) applying equation 4, given by $$S_D^{(mn)} = \overline{M}_A^{(n)} \cdot M \cdot M_{SCN}^{(1)} \cdot S_G^{(m)},$$

to reconstruct images, $I^{(out)}$, pixel by pixel for each incident Stokes vector;

i) for each image, calculate the image quality measure of choice, for example SNR as defined in equation 7, given by $$SN = (SNR)^{-1} = \frac{stdv(I^{(out)})}{mean(I^{(out)})};$$

and j) display the image with best value of the image quality measure.

20. The method according to claim 19 wherein said object is an inanimate object, and wherein said step of focusing light onto said object includes directing light through a focusing lens onto said object and capturing and processing images propagating back through said focusing lens reflected from said object.

21. The method according to claim 20 wherein said object is an animate object, and wherein said step of focusing light onto said object includes directing light through a focusing lens onto said object and capturing and processing images propagating back through said focusing lens reflected from said object.

22. The method according to claim 19 wherein said object is a patients eye, and wherein said confocal scanning laser microscope is a confocal scanning laser ophthalmoscope (in this case the objective of the scanning laser microscope is replaced by the optics of the eye), and wherein the step of focusing light onto said eye includes directing light into the eyeball and capturing and processing images propagating back through said eyeball.

23. An optical scanning apparatus for producing images of an object, comprising:
   a) a light source for producing a light beam;
   b) polarization generator for producing selected polarization states in the light beam upon passage of the light beam through said polarization generator to produce a selectively polarized light beam;
   c) scanning mechanism for receiving the selectively polarized light beam and spatially scanning the selectively polarized light beam in two dimensions across an object point by point;
   d) polarization analyzer for transmitting light beams of selected polarization, including directing and focusing optics for directing the reflected light beams reflected point by point from the object to said polarization analyzer;
   e) detector and light shaping and focusing optics for directing and focusing the reflected or transmitted light beams of selected polarization onto said detector;
   f) computer processor connected to said detector, said computer processor including image analysis means for processing signals from said detector due to the reflected light beams of selected polarization detected by said detector and producing therefrom images of the object; and
   g) display means for displaying an image of the object produced by said processing means.

24. The apparatus according to claim 23 wherein said light source is a laser for producing coherent or partially coherent light beams.

25. The apparatus according to claim 23 wherein said light shaping and focusing means includes a beam splitter positioned to transmit the selectively polarized light beam from said polarization generation means to said scanning means and to direct the light beams reflected point by point from the object to the polarization analyzer means, and wherein said light shaping and focusing means includes a confocal pinhole and focusing lens positioned between said detection means and said polarization analyzer means for focusing light beams reflected point by point from the object and having the selected polarization onto said detection means.

26. The apparatus according to claim 23 wherein said polarization generator means includes a linear polarizer and a rotatable quarter wave plate, and wherein said polarization analyzer means includes a linear polarizer and a rotatable quarter wave plate.

27. The apparatus according to claim 23 wherein said polarization generator includes an electro-optical device for polarizing the incident light beam, and wherein said polarization analyzer includes an electro-optical device.

28. The apparatus according to claim 27 wherein said electro-optical devices are one of a liquid crystal modulator and a photoelastic modulator.

29. The apparatus according to claim 23 wherein the object is a person's eye and said apparatus is a scanning laser ophthalmoscope or confocal scanning laser ophthalmoscope, and including positioning means for holding a person's head in position with the person's eye positioned so the light beam having selected polarization is scanned across the eye.

30. The apparatus according to claim 23 including focusing optics for receiving the selectively polarized light beams from said scanning means and focussing the selectively polarized light beams onto the object, and wherein said apparatus is a confocal scanning laser microscope or a scanning laser microscope.

31. An optical scanning apparatus for producing images of an object, comprising:
   a) a light source for producing a light beam;
   b) polarization generator means for producing selected polarization states in the light beam upon passage of the light beam through said polarization generator means to produce a selectively polarized light beam;
   c) a beam splitter for transmitting the selectively polarized light beam;
   d) scanning means for receiving the selectively polarized light beam from said beam splitter and spatially scanning the selectively polarized light beam in two dimensions across an object point by point and receiving light beams reflected back from different positions on the object and directing the reflected light beams to said beam splitter;
   e) polarization analyzer means positioned to receive reflected light beams reflected from said beam splitter for transmitting reflected light beams of selected polarization;
   f) detection means and light shaping and focusing means for directing and focusing the reflected light beams of selected polarization onto said detection means;
   g) computer processing means connected to said detection means, said computer processing means including image analysis means for processing signals from the detector due to the reflected light beams of selected polarization detected by said detection means and producing therefrom images of the object; and
   h) display means for displaying an image of the object produced by said processing means.

32. The apparatus according to claim 31 wherein said light source is a laser for producing coherent or partially coherent light beams.

33. The apparatus according to claim 31 wherein said polarization generator means includes a linear polarizer and a rotatable quarter wave plate, and wherein said polarization analyzer means includes a linear polarizer and a rotatable quarter wave plate.

34. The apparatus according to claim 31 wherein said light shaping and focusing means for directing and focusing the reflected light beams of selected polarization onto said detection means includes a confocal pinhole and focusing lens positioned between said detection means and said polarization analyzer means for focusing light beams reflected point by point from the object and having the selected polarization onto said detection means.

35. The apparatus according to claim 32 wherein the object is a person's eye and said apparatus is a confocal scanning laser ophthalmoscope, and including positioning means for holding a person's head in position with the person's eye positioned so said laser beam is scanned across the eye.

36. The apparatus according to claim 34 including light beam directing and focusing optics for receiving said selectively polarized light beam from said scanning means and directing and focussing said selectively polarized coherent light beam onto the object, and wherein said apparatus is a confocal scanning laser microscope.

37. A method for producing images of an object or region of interest of the object, comprising the steps of:
- a) producing an incident beam of light in a pre-selected polarization state and scanning said incident beam of light point by point across and/or along an object or region of interest of the object;
- b) detecting light intensity signals corresponding to beams of light in a pre-selected number of polarization states reflected or transmitted point by point from the object or region of interest of the object and storing electronic signals corresponding to the detected light intensity signals;
- c) repeating steps a) and b) for an effective number of pre-selected polarization states of the incident beam of light;
- d) constructing a spatially resolved matrix of the object point by point from the detected light intensity signals and from said spatially resolved matrix constructing spatially resolved images of the object or region of interest of the object for a set of theoretical polarization states of the incident beam of light in addition to those input states generated in the incident beam of light, said matrix being selected to describe the effect of the object on the polarization properties of light;
- e) characterizing image quality of each image in accordance with an effective image quality parameter and based upon said characterization selecting a best image of said object or region of said object; and
- f) visually displaying said best image.

38. A method for producing images of an object or region of interest of the object, comprising the steps of:
- a) producing an incident beam of light in a pre-selected polarization state and scanning said incident beam of light point by point across an object or region or along an object or a region of interest of the object by moving the object with respect to the incident beam or by moving the object in 1 dimension with respect to the incident beam and scanning the beam in a perpendicular direction with respect to the object;
- b) detecting light intensity signals corresponding to beams of light reflected or transmitted point by point from the object or region of interest of the object and storing electronic signals corresponding to the detected light intensity signals;
- c) repeating steps a) and b) for an effective number of pre-selected polarization states of the incident beam of light;
- d) constructing a spatially resolved vector of the object point by point from the detected light intensity signals and from said spatially resolved vector constructing spatially resolved images of the object or region of interest of the object for a set of theoretical polarization states of the incident beam of light in addition to those input states generated in the incident beam of light, said vector comprised of independent elements of a matrix being selected to describe the effect of the object on the polarization properties of light;
- e) characterizing image quality of each image in accordance with an effective image quality parameter and based upon said characterization selecting a best image of said object; and
- f) visually displaying said best image.

39. A method for producing images of an object using scanning laser microscopy or macroscopy, in transmission mode, comprising the steps of:
- a) calibrating a scanning laser microscope or macroscope modified to include a polarization generator and a polarization analyzer to obtain a Mueller matrix $M_{SCN}^{(1)}$, of the instrument in the incoming direction, wherein a matrix of 16 intensity values results from intensity measurements with a rotating ¼ wave plate located in said generator positioned in each of four positions including 45 degrees, 0 degrees, 30 degrees and 60 degrees, while a ¼ wave plate located in said analyzer is placed in each of the same four positions;
- b) placing said object in said modified confocal scanning apparatus and focusing light onto said object and recording sixteen gray scale images with the object in place for each of four generator states with a ¼ wave plate at 45, 0, 30 and 60 degrees combined with each of the four analyzer states ¼ wave plate at 45, 0, 30 and 60 degrees;
- c) placing said sixteen grey scale values for each pixel into a spatially resolved matrix, $I^{(mn)}$, which is a first element of a Stokes vector, $$S_D^{(mn)}$$

reaching the photodetector;
- d) from $I^{(mn)}$ calculate $M_{out}$ from equation 2, given by $$\begin{pmatrix} I^{(1\_1)} & I^{(2\_1)} & I^{(3\_1)} & I^{(4\_1)} \\ I^{(1\_2)} & I^{(2\_2)} & I^{(3\_2)} & I^{(4\_2)} \\ I^{(1\_3)} & I^{(2\_3)} & I^{(3\_3)} & I^{(4\_3)} \\ I^{(1\_4)} & I^{(2\_4)} & I^{(3\_4)} & I^{(4\_4)} \end{pmatrix} = M_A \cdot M_{OUT};$$

- e) from equation 5, given by $$M = M_{OUT} \cdot (M_G)^{-1} \cdot (M_{SCN}^{(1)})^{-1},$$

calculate M, the spatially resolved Mueller matrix of the object;
- f) choosing values of an incident Stokes vector, $S_{IN}$, around a Poincaré sphere in predetermined increments of $\chi$ and $\phi$ which represent, respectively, the azimuth and ellipticity of the incident Stokes vector on the Poincaré sphere;
- g) applying equation 6, given by $$\begin{pmatrix} I^{(OUT)} \\ S_1^{(OUT)} \\ S_2^{(OUT)} \\ S_3^{(OUT)} \end{pmatrix} = \begin{pmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{pmatrix} \cdot \begin{pmatrix} 1 \\ \cos(2\chi)\cdot\cos(2\varphi) \\ \sin(2\chi)\cdot\cos(2\varphi) \\ \sin(2\varphi) \end{pmatrix}$$

$$= M \cdot S_{IN},$$

to reconstruct images, $I^{(out)}$, pixel by pixel for each incident Stokes vector;
- h) for each image, calculating the image quality measure of choice, for example SNR as defined in equation 7, given by $$SN = (SNR)^{-1} = \frac{stdv(I^{(out)})}{mean(I^{(out)})};$$

and i) displaying the image with best value of the image quality measure.

40. An optical scanning apparatus for producing images of an object, comprising;

a) a light source for producing a light beam;

b) polarization generator means for producing selected polarization states in the light beam upon passage of the light beam through said polarization generator means to produce a selectively polarized light beam;

c) scanning means for receiving the selectively polarized light beam and spatially scanning the selectively polarized light beam in two dimensions across an object point by point scanning the sample with respect to the laser beam or scanning the beam in 1 or 2 dimensions and the sample in the perpendicular direction;

d) polarization analyzer means for transmitting light beams of selected polarization, including directing and focusing optics for directing the reflected light beams reflected point by point from the object to said polarization analyzer means;

e) detection means and light shaping and focusing means for directing and focusing the reflected light beams of selected polarization onto said detection means;

f) computer processing means connected to said detection means, said computer processing means including image analysis means for processing signals from said detector due to the reflected light beams of selected polarization detected by said detection means and producing therefrom images of the object; and g) display means for displaying an image of the object produced by said processing means.

* * * * *